US009919288B2

(12) United States Patent
Du et al.

(10) Patent No.: US 9,919,288 B2
(45) Date of Patent: Mar. 20, 2018

(54) ZIF-CONTAINING ADSORBENT MATERIALS AND USES THEREOF

(71) Applicant: ExxonMobil Research and Engineering Company, Annandale, NJ (US)

(72) Inventors: Yi Du, Coopersburg, PA (US); Kanmi Mao, Clinton, NJ (US); Bradley Wooler, Quakertown, PA (US); Arun K. Sharma, Hellertown, PA (US); Doug F. Colmyer, Spinnerstown, PA (US); Frank C. Wang, Annandale, NJ (US); Simon C. Weston, Annandale, NJ (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 0 days.

(21) Appl. No.: 15/175,071

(22) Filed: Jun. 7, 2016

(65) Prior Publication Data

US 2016/0367962 A1    Dec. 22, 2016

Related U.S. Application Data

(60) Provisional application No. 62/180,639, filed on Jun. 17, 2015, provisional application No. 62/304,369, filed on Mar. 7, 2016.

(51) Int. Cl.
| | |
|---|---|
| *B01J 20/18* | (2006.01) |
| *B01D 15/00* | (2006.01) |
| *B01J 20/22* | (2006.01) |
| *B01J 20/26* | (2006.01) |
| *C07C 7/13* | (2006.01) |
| *C07C 29/76* | (2006.01) |
| *C10L 1/02* | (2006.01) |
| *C12P 5/02* | (2006.01) |
| *C12P 7/06* | (2006.01) |
| *C12P 7/16* | (2006.01) |

(52) U.S. Cl.
CPC ............. *B01J 20/18* (2013.01); *B01D 15/00* (2013.01); *B01J 20/226* (2013.01); *B01J 20/267* (2013.01); *C07C 7/13* (2013.01); *C07C 29/76* (2013.01); *C10L 1/02* (2013.01); *C12P 5/02* (2013.01); *C12P 7/06* (2013.01); *C12P 7/16* (2013.01); *B01J 2220/44* (2013.01); *C10L 2290/12* (2013.01); *C10L 2290/26* (2013.01); *C10L 2290/542* (2013.01); *Y02E 50/343* (2013.01)

(58) Field of Classification Search
None
See application file for complete search history.

(56) References Cited

U.S. PATENT DOCUMENTS

| | | | |
|---|---|---|---|
| 8,142,745 | B2 | 3/2012 | Reyes et al. |
| 8,636,969 | B2 | 1/2014 | Weston et al. |
| 8,907,102 | B2 | 12/2014 | Weston et al. |
| 8,920,541 | B2 | 12/2014 | Ni et al. |
| 2008/0227634 | A1 | 9/2008 | Muller et al. |
| 2009/0211440 | A1 | 8/2009 | Reyes et al. |
| 2010/0012656 | A1 | 1/2010 | Stone |
| 2013/0259783 | A1 | 10/2013 | Ni et al. |
| 2013/0259792 | A1 | 10/2013 | Weston et al. |
| 2014/0212940 | A1 | 7/2014 | Yang et al. |
| 2014/0284277 | A1 | 9/2014 | Medoff et al. |

FOREIGN PATENT DOCUMENTS

| | | |
|---|---|---|
| WO | 2008095896 A1 | 8/2008 |
| WO | 2010012656 A1 | 2/2010 |

OTHER PUBLICATIONS

PCT/US2016/0361783 International Search Report and Written Opinion dated Sep. 9, 2016.
Cooper et al., "Dynamic Nuclear Polarization NMR Spectroscopy Allows High-Throughput Characterization of Microporous Organic Polymers", Journal of the American Chemical Society, Sep. 12, 2013, pp. 9028-9035, vol. 134(41), ACS Publications.
Dong et al., "Synthesis of an organophilic ZIF-71 membrane for pervaporation solvent separation", Chem. Comm., 2013, pp. 1196-1198, vol. 49, RSC Publishing.
Zhang et al., "Biofuel purification in zeolitic imidazolate frameworks: the significant role of functional groups", Physical Chemistry Chemical Physics, 2014, pp. 9643-9655, vol. 16, RSC Publishing.
Gee et al., "Adsorption and Diffusion of Small Alcohols in Zeolitic Imidazolate Frameworks ZIF-8 and ZIF-90", Journal of Physical Chemistry C, Jul. 17, 2013, pp. 3169-3176, vol. 117(6), ACS Publications.
Zhang et al., "Alcohol and water adsorption in zeolitic imidazolate frameworks", Chemical Communications, 2013, pp. 3245-3247, vol. 49, RSC Publishing.
Liu et al., "An Organophilic Pervaporation Membrane Derived from Metal-Organic Framework Nanoparticles for Efficient Recovery of Bio-Alcohols", Angewandte Chemie International Edition, 2011, pp. 10636-10639, vol. 50(45), Wiley-VCH Verlag GmbH & Co., KGaA, Weinheim.
Zhang et al., Adsorption of C1—C4 Alcohols in Zeolitic Imidazolate Framework-8: Effects of Force Fields, Atomic Charges, and Framework Flexibility, Journal of Physical Chemistry C, 2013, pp. 25628-25635, vol. 117(48), ACS Publications.
Woodward et al., "Swellable, Water- and Acid-Tolerant Polymer Sponges for Chemoselective Carbon Dioxide Capture", Journal of the American Chemical Society, 2014, pp. 9028-9035, vol. 136(25), ACS Publications.

(Continued)

*Primary Examiner* — Yun Qian
(74) *Attorney, Agent, or Firm* — Andrew T. Ward

(57) ABSTRACT

Adsorbent materials comprising a ZIF material and cross-linked polymer are provided herein. Methods of separating organic compounds from an aqueous solution or a non-aqueous solution and biofuel production processes using the adsorbent material are also provided herein.

7 Claims, 18 Drawing Sheets

(56) References Cited

OTHER PUBLICATIONS

Sano et al., "Separation of ethanol/water mixture by silicalite membrane on pervaporation", Journal of Membrane Science, 1994, pp. 221-228, vol. 95, Elsevier.

Okeeffe et al., "The Reticular Chemistry Structure Resource (RCSR) Database of, and Symbols for, Crystal Nets", Accounts of Chemical Research, Dec. 2008, pp. 1782-1789, vol. 41(12), ACS Publications.

Label of the carbon atoms $^{13}C$-$^1H$ 2D NMR of ZIF-7-np $^{13}C$-$^1H$ 2D NMR of ZIF-7-lp with ethanol

*In situ* XRD patterns of ZIF-7 w. different 1-Pentanol loadings

ZIF-CONTAINING ADSORBENT MATERIALS AND USES THEREOF

CROSS-REFERENCE TO RELATED APPLICATIONS

This application claims priority to U.S. Provisional Application Ser. No. 62/304,369 filed on Mar. 7, 2016 and provisional application 62/180,639 filed on Jun. 17, 2015, herein incorporated by reference in its entirety.

FIELD

The present invention relates to an adsorbent material comprising a zeolitic imidazolate framework (ZIF) material and a cross-linked polymer, which can be used for separating organic compounds from an aqueous or a non-aqueous solution.

BACKGROUND

With the ever increasing demand for energy coupled with the depletion of traditional non-renewable energy sources (i.e., fossil fuels), there is a strong need for development of alternate fuels, particularly "renewable fuels." Thus, there is much interest in the production of biofuel. Biofuels are viable alternatives to fossil fuels (e.g., petroleum, natural gas) because they comprise a wide range of liquid, solid biomass, or biogas fuels that are in some way derived from a carbon source that can be rapidly replenished (including for example hydrocarbons derived from or produced by biological organisms).

During the production of biofuel, a large quantity of water and alcohols are produced requiring adequate and cost-effective separation. For example, one of the leading biofuel production methods is enzymatic hydrolysis and fermentation, which generates alcohols, such as ethanol and isobutanol at lower concentrations (e.g., ~0.5-10 wt. %) in water. In addition to the desirability of recovering the low concentration alcohols for use in biofuels, it is also important to separate the lower concentration alcohols from water during the course of biofuel production because the enzymes utilized can lose activity in the presence of alcohols at a concentration of ~0.5-10 wt. %. However, conventional separation methods, such as distillation, are not economical due to the large amount of water present. Furthermore, simultaneous separation of the alcohol product from the reactor is desirable because the process can proceed in a substantially continuous manner thereby reducing downtime and improving productivity.

Thus, various porous materials (e.g., activated carbon, zeolites) have been investigated for separation of alcohol-water mixtures. One class of compounds of interest is metal-organic frameworks (MOFs), which comprise various inorganic clusters and organic linkers resulting in a wide range of surface areas and porosities. A subfamily of MOFs is zeolitic imidazolate frameworks (ZIFs), which have zeolite-like topology and are constructed by using tetrahedral transition metal ions and imidazolate-based bridge ligands. While most studies utilizing ZIF materials have focused on gas adsorption and separation, some ZIF materials have been studied for separation of water-alcohol mixtures, such as in membrane separation. For example, Liu, X.-L. et al. studied membranes containing ZIF-8 nanoparticles and ZIF-7 nanoparticles for pervaporation recovery of isobutanol from aqueous solutions and found that the ZIF-8 membrane had a higher isobutanol permeance compared to the ZIF-7 membrane ("isotherms of ZIF-7 nanoparticles show insignificant adsorption of isobutanol"). *Angew. Chem. Int. Ed.*, 50: 10636-10639, 10638 (2011). Dong, X. et al. report alcohol (methanol and ethanol)-water separation with a ZIF-71 membrane. *Chem. Commun.*, 49: 1196-1198 (2013). Additionally, U.S. Patent Publication No. 2014/0212940 reports ZIF-containing (e.g., ZIF-4, ZIF-5, ZIF-7, ZIF-8) membranes and processes for removing alcohols from water.

Nonetheless, as noted by Dong, X. et al., within the field of liquid mixture separation, there are formidable challenges associated with screening of suitable ZIF materials due to, for example, the many properties associated with ZIFs, such as pore size, structure, surface chemistry, and thermal and chemical stability. Furthermore, it remains difficult for current adsorbent materials to selectively adsorb trace amounts of organic compounds, such as alcohols, from liquid mixtures. Therefore, there is a need to provide additional adsorbent materials with both improved adsorption capacity and selectivity for organic compounds, such as methanol, ethanol, propanol and butanol, in water, which can be used in separation processes during the production of biofuel.

SUMMARY

It has been found that an adsorption material for separation of organic compounds (e.g., alcohols) from a solution, such as an aqueous solution, can be achieved by providing an adsorbent material comprising a ZIF material and a cross-linked polymer.

Thus, in one aspect, embodiments of the invention provide an adsorbent material comprising: a ZIF material comprising linkers selected from the group consisting of an optionally substituted benzimidazole linker, an optionally substituted azabenzimidazole linker, an optionally substituted purine linker, and any combination thereof; and a cross-linked polymer comprising multiple monomers containing a moiety corresponding in structure to Formula (I):

wherein $R^1$ and $R^2$ are independently selected from the group consisting of hydrogen, $C_1$-$C_6$-alkyl, aryl, $C(R^3)_3$ in which each $R^3$ is independently hydrogen or aryl; or, taken together, $R^1$ and $R^2$ form a monocyclic or polycyclic aromatic hydrocarbon.

In still another aspect, embodiments of the invention provide an adsorbent material comprising a ZIF material having: (i) an adsorptive loading ratio for methanol over water of at least about 20 at about 30° C. and at least about 10 at about 75° C.; (ii) an adsorptive loading ratio for ethanol over water of at least about 25 at about 30° C. and at least about 85 at about 75° C.; and/or (iii) an adsorptive loading ratio for 1-pentanol over water of at least about 20 at about 30° C.; and a cross-linked polymer having an adsorptive loading ratio for isobutanol over water of at least about 1 at about 30° C.

In still another aspect, embodiments of the invention provide a method for separating at least one organic compound from an aqueous solution, wherein the method comprises: contacting the aqueous solution with an adsorbent material comprising: a ZIF material comprising linkers selected from the group consisting of an optionally substituted benzimidazole linker, an optionally substituted azabenzimadazole linker, an optionally substituted purine linker, and any combination thereof; and a cross-linked polymer comprising multiple monomers containing a moiety corresponding in structure to Formula (I):

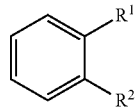
(I)

wherein $R^1$ and $R^2$ are independently selected from the group consisting of hydrogen, $C_1$-$C_6$-alkyl, aryl, $C(R^3)_3$ in which each $R^3$ is independently hydrogen or aryl; or, taken together, $R^1$ and $R^2$ form a monocyclic or polycyclic aromatic hydrocarbon.

In still another aspect, embodiments of the invention provide a method of producing biofuel, wherein the method comprises: hydrolyzing a biomass to form sugars; fermenting the sugars to produce an aqueous solution comprising one or more alcohols; and separating the one or more alcohols from the aqueous solution by contacting the aqueous solution with the adsorbent material described herein.

Other embodiments, including particular aspects of the embodiments summarized above, will be evident from the detailed description that follows.

DETAILED DESCRIPTION

Figure 1:
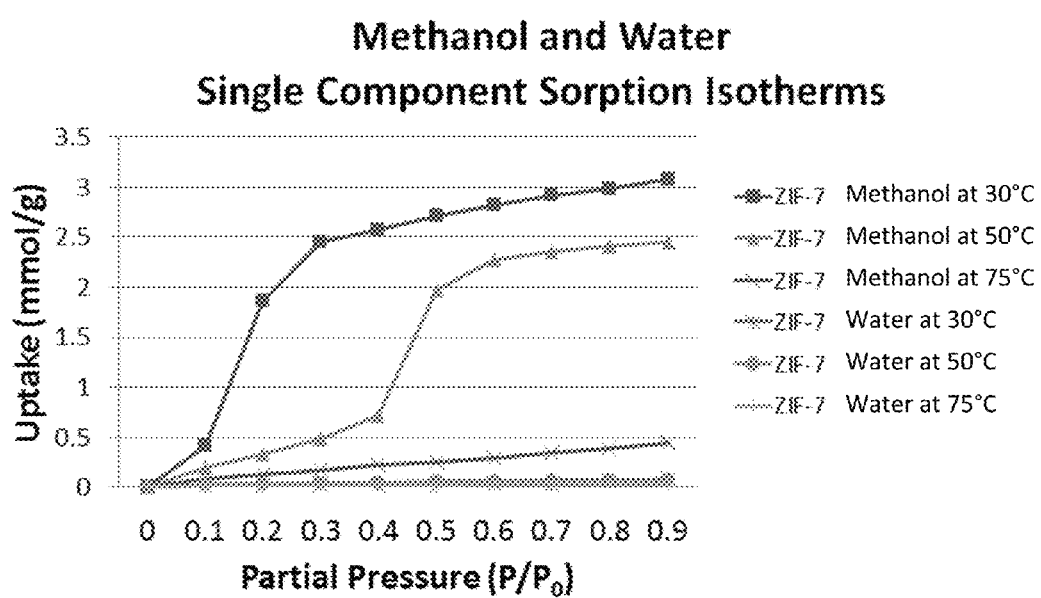
FIG. 1 illustrates methanol and water single component adsorption isotherms for ZIF-7.

In various aspects of the invention, adsorbent materials, methods of separating organic compounds and biofuel production processes using the adsorbent materials are provided.

I. Definitions

To facilitate an understanding of the present invention, a number of terms and phrases are defined below.

As used in the present disclosure and claims, the singular forms "a," "an," and "the" include plural forms unless the context clearly dictates otherwise.

Wherever embodiments are described herein with the language "comprising," otherwise analogous embodiments described in terms of "consisting of" and/or "consisting essentially of" are also provided.

The term "and/or" as used in a phrase such as "A and/or B" herein is intended to include "A and B", "A or B", "A", and "B".

The terms "substituent", "radical", "group", "moiety" and "fragment" may be used interchangeably.

As used herein, the term "adsorption" includes physisorption, chemisorption, and condensation onto a solid material and combinations thereof.

As used herein, the term "alkane" refers to non-aromatic saturated hydrocarbons with the general formula $C_nH_{(2n+2)}$, where n is 1 or greater. An alkane may be straight chained or branched. Examples of alkanes include, but are not limited to methane, ethane, propane, butane, pentane, hexane, heptane and octane. "Alkane" is intended to embrace all structural isomeric forms of an alkane. For example, butane encompasses n-butane and isobutane; pentane encompasses n-pentane, isopentane and neopentane.

As used herein, the term "alkyl" refers to a saturated hydrocarbon radical of 1 to about 12 carbon atoms (i.e. $C_1$-$C_{12}$-alkyl) in length, such as, but not limited to, methyl, ethyl, propyl, butyl, pentyl, hexyl, heptyl, octyl, decyl, and so forth. The alkyl group may be straight-chain or branched-chain. "Alkyl" is intended to embrace all structural isomeric forms of an alkyl group. For example, as used herein, propyl encompasses both n-propyl and isopropyl; butyl encompasses n-butyl, sec-butyl, isobutyl and tert-butyl.

As used herein, the term "alkene" refers to a branched or unbranched unsaturated hydrocarbon having one or more carbon-carbon double bonds. A simple alkene comprises the general formula $C_nH_{2n}$, where n is 2 or greater. Examples of alkenes include, but are not limited to ethene, propene, butene, pentene, hexene and heptene. "Alkene" is intended to embrace all structural isomeric forms of an alkene. For example, butene encompasses but-1-ene, (Z)-but-2-ene, etc.

As used herein, the term "alkenyl" refers to a branched or unbranched unsaturated hydrocarbon radical having 2 to 12 carbon atoms (i.e., $C_2$-$C_{12}$-alkenyl) and having one or more carbon-carbon double bonds. Examples of alkenyls include, but are not limited to ethenyl (vinyl), 2-propenyl, 3-propenyl, 1,4-pentadienyl, 1,4-butadienyl, 1-butenyl, 2-butenyl and 3-butenyl. "Alkenyl" is intended to embrace all structural isomeric forms of an alkenyl. For example, butenyl encompasses 1,4-butadienyl, 1-butenyl, 2-butenyl and 3-butenyl, etc.

As used herein, the term "alcohol" refers to a hydroxy group (—OH) bound to a saturated carbon atom (i.e., an alkyl). Examples of the alkyl portion of the alcohol include, but are not limited to propyl, butyl, pentyl, hexyl, iso-propyl, iso-butyl, sec-butyl, tert-butyl, etc. The alcohol may be straight or branched. "Alcohol" is intended to embrace all structural isomeric forms of an alcohol. Examples of alcohols include, but are not limited to methanol, ethanol, propanol, isopropanol, glycerol, butanol, isobutanol, n-butanol, tert-butanol, pentanol and hexanol. As used herein, the term "butanol" encompasses n-butanol, isobutanol and tert-butanol. As used herein, the term "propanol" encompasses 1-propanol and isopropanol. Additionally or alternatively, the alcohol may be independently substituted with a $C_1$-$C_8$-alkyl. For example, butanol may be substituted with a methyl group, such as, but not limited to 2-methyl-1-butanol and 3-methyl-2-butanol.

As used herein, the term "aryl" refers to any monocyclic or polycyclic cyclized carbon radical containing 6 to 14 carbon ring atoms, wherein at least one ring is an aromatic hydrocarbon. Examples of aryls include, but are not limited to phenyl, naphthyl, and indolyl.

As used herein, the term "aromatic hydrocarbon" refers to a cyclic hydrocarbon having a delocalized conjugated π system. The aromatic hydrocarbon may be monocyclic or polycyclic (e.g., bicyclic, tricyclic, etc.). In the polycyclic aromatic hydrocarbon at least one ring is aromatic, where the aromatic ring may be attached to another aromatic ring (e.g., naphthyl) or attached to a non-aromatic cycloalkyl or heterocyclyl radical in a fused or pendant or bridged manner. An example of a polycyclic aromatic hydrocarbon wherein an aromatic ring is attached to a non-aromatic cycloalkyl includes one or more benzene rings attached to a 4-10-membered cycloalkyl. In particular, 2 benzene rings fused to a bridged 8-membered cycloalkyl.

As used herein, the term "hydrogen" refers to a hydrogen radical and may be depicted as —H.

As used herein, the term "halo" refers fluoro (—F), chloro (—Cl), bromo (—Br), or iodo (—I).

As used herein, the term "nitro" refers to —$NO_2$.

As used herein, the term "cyano" refers to a radical of the formula —C≡N.

As used herein, the term "phenyl" refers to a cyclic group of atoms with the formula $C_6H_5$—.

As used herein, the term "naphthyl" refer to a monovalent bicyclic aromatic hydrocarbon radical consisting of a fused pair of benzene rings.

As used herein the term "indolyl" refers to a monovalent heterocyclic aromatic radical consisting of a six-membered benzene ring fused to a five-membered nitrogen-containing pyrrole ring.

As used herein, "zeolitic imidazolate framework" (or "ZIF") materials refer to crystalline microporous structures having frameworks (or topologies) commonly found in zeolites and/or in other crystalline materials wherein each vertex of the framework structure is comprised of a single metal ion and each pair of connected adjacent vertices of the framework structure is linked by nitrogen atoms of an imidazolate anion or its derivative. The frameworks (or topologies) as disclosed herein can comprise any of the networks defined in the Atlas of Zeolite Structure Types and the Reticular Chemistry Structure Resource (RCSR) Database known in the literature.

As used therein, the term "biofuel" refers to any fuel derived from a biological source or biomass.

As used herein, the term "biomass" refers to a carbon source derived from biological material, such as, but not limited to plant matter, microbe, a photosynthetic microorganism, such as a microalga or cyanobacterium, fungus, living cell, animal matter, waste products from industry, agriculture, forestry, and households. Examples of plant matter include, but are not limited to corn, sugar cane and switchgrass. For example, the photosynthetic microorganism can be a microalga that is a species of *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Picochlorum, Platymonas, Pleurochrysis, Pleurococcus, Prototheca, Pseudochlorella, Pseudoneochloris, Pyramimonas, Pyrobotrys, Scenedesmus, Schizochlamydella, Skeletonema, Spyrogyra, Stichococcus, Tetrachorella, Tetraselmis, Thalassiosira, Viridiella,* or *Volvox.* Alternatively, the photosynthetic microorganism can be a cyanobacterium and can be a species of *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactyococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Thermosynechococcus, Tolypothrix, Trichodesmium, Tychonema* or *Xenococcus.* An example of animal matter is animal manure, such as cow manure. Examples of waste products include, but are not limited to fermentation waste, straw, lumber, sewage, garbage, and food leftovers. Biomass also includes sources of carbon, such as carbohydrates (e.g., monosaccharides, disaccharides, or polysaccharides).

As used herein the term "organic compounds" refers to compounds containing carbon atoms, such as, but not limited to alkanes, alkenes, alcohols, aldehydes, esters, and aromatic compounds.

As used herein, the term "porosity" refers to a measure of the void spaces in a material, and is measured herein as percent between zero and 100%.

As used herein, the term "microporous" refers to solid materials having pores with a diameter less than 2 nm.

II. Adsorbent Material

In a first embodiment an adsorbent material is provided comprising a ZIF material and a cross-linked polymer.

A. ZIF Material

Zeolitic imidazolate frameworks or ZIFs have properties similar to to inorganic zeolitic materials. ZIFs are based on [M(IM)$_2$] tetrahedral bonds in which IM is an imidazolate type linking moiety and M is a transition metal. Each M is tetrahedrally coordinated to four IM, and each IM is coordinated to two M. These materials are generally referred to as zeolitic imidazolate frameworks or ZIFs since the angle formed by imidazolates (IMs) when bridging transition metals is similar to the 145° angle of the Si—O—Si bond in zeolites. ZIF materials are of particular interest as adsorption materials because they can exist in a narrow pore (np) phase and a large pore (lp) phase. Upon adsorption the ZIF material can perform a phase change thereby displaying on/off porosity. For example, ZIF-7 has a surface area of ≤10 m²/g in the np phase and an estimated surface area of >~300 m²/g in the lp phase. In ZIF-7's SOD framework and benzimidazole linkers, the 6-membered windows function as cages and adsorption sites, and the rotation of linkers create on/off porosity affecting adsorption.

The transition metal may comprise, for example, at least one of the following group of metals: Sc, Ti, V, Cr, Mn, Fe, Co, Ni, Cu, Zn, Y, Zr, Nb, Mo, Tc, Ru, Rh, Pd, Ag, Cd, Lu, Hf, Ta, W, Re, Os, Ir, Pt, Au, Hg, Lr, Rf, Db, Sg, Bh, Hs, Mt, Ds, Rg, and Uub. Particularly, the transition metal is Zn.

Additionally or alternatively, the ZIF material may have a framework type selected from the following group of framework types: ABW, ACO, AEI, AEL, AEN, AET, AFG, AFI, AFN, AFO, AFR, AFS, AFT, AFX, AFY, AHT, ANA, APC, APD, AST, ASV, ATN, ATO, ATS, ATT, ATV, AWO, AWW, BCT, BEA, BEC, BIK, BOG, BPH, BRE, CAG, CAN, CAS, CDO, CFI, CGF, CGS, CHA, CHI, CLO, CON, CRB, CZP, DAC, DDR, DFO, DFT, DIA, DOH, DON, EAB, EDI, EMT, EON, EPI, ERI, ESV, ETR, EUO, EZT, FAR, FAU, FER, FRA, FRL, GIS, GIU, GME, GON, GOO, HEU, IFR, THW, ISV, ITE, ITW, TWR, IWV, IWW, JBW, KFI, LAU, LCS, LEV, LIO, LIT, LOS, LOV, LTA, LTL, LTN, MAR, MAZ, MEI, MEL, MEP, MER, MFI, MFS, MON, MOR, MOZ, MSE, MSO, MTF, MTN, MTT, MTW, MWW, NAB, NAT, NES, NON, NPO, NSI, OBW, OFF, OSI, OSO, OWE, PAR, PAU, PHI, PON, POZ, RHO, RON, RRO, RSN, RTE, RTH, RUT, RWR, RWY, SAO, SAS, SAT, SAV, SBE, SBS, SBT, SFE, SFF, SFG, SFH, SFN, SFO, SGT, SIV, SOD, SOS, SSY, STF, STI, STT, SZR, TER, THO, TON, TSC, TUN, UEI, UFI, UOZ, USI, UTL, VET, VFI, VNI, VSV, WEI, WEN, YUG, ZNI, and ZON. Additionally or alternatively, the ZIF material may have a framework type selected from the following group of RCSR topologies: cag, coi, dft, dia, dia-c, dia-c-b, fes, frl, gar, gis, mab, med, mog, moz, neb, nog, pcb, poz, qtz, srs-c-b, ths-c-b, zea, zeb, zec, zni, and zni-b. A person of ordinary skill in the art knows how to make the aforementioned frameworks. For example, see the references provided in the International Zeolite Association's database of zeolite structures found at www.iza-structure.org/databases and the references provided in O'Keeffe, M.; Peskov, M. A.; Ramsden, S. J.; Yaghi, O. M. *Accts. Chem. Res.*, 41:1782-1789 (2008). Particular examples of these framework types can include CRB, DFT, CAG, SOD, MER, RHO, ANA, LTA, DIA, ZNI, GME, LCS, FRL, GIS, POZ, and MOZ.

Exemplary ZIF materials include, but are not limited to ZIF-1, ZIF-2, ZIF-3, ZIF-4, ZIF-5, ZIF-6, ZIF-7, ZIF-8, ZIF-9, ZIF-10, ZIF-11, ZIF-12, ZIF-14, ZIF-20, ZIF-21, ZIF-22, ZIF-23, ZIF-25, ZIF-60, ZIF-61, ZIF-62, ZIF-63, ZIF-64, ZIF-65, ZIF-66, ZIF-67, ZIF-68, ZIF-69, ZIF-70, ZIF-71, ZIF-72, ZIF-73, ZIF-74, ZIF-75, ZIF-76, ZIF-78, ZIF-90, ZIF-91, ZIF-92, ZIF-93, ZIF-96, ZIF-97, ZIF-100, EMM-19 and EMM-19*. EMM-19 and EMM-19* can be formed by methods described in U.S. Pat. Nos. 8,636,969, 8,907,102, and 8,920,541, each of which is incorporated by reference in its entirety. As described in U.S. Pat. No. 8,636,969, removal of substantially all of the acetonitrile from an acetonitrile-exchanged EMM-19 sample followed by treatment with N₂ gas resulted in EMM-19*. Thus, EMM-19* is a modified version of EMM-19, which is still chemically Zn(5-azabenzimidazole)₂ having SOD framework, but exhibiting different activity than EMM-19. Particularly, the ZIF material is selected from the group consisting of ZIF-7, ZIF-22, EMM-19 and EMM-19*. In particular, the ZIF material is ZIF-7.

Additionally or alternatively, the ZIF material may have a structure or a basic structural unit corresponding to the following linker formulas:

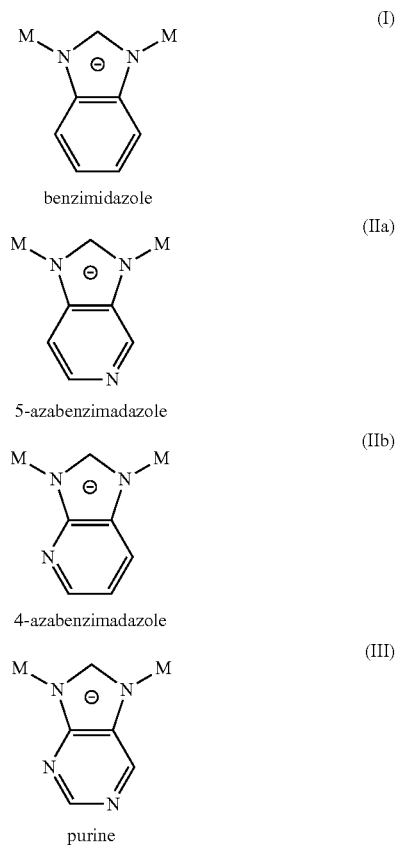

wherein M can independently be one of the transition metals listed above. In particular, the ZIF material can include benzimidazole linkers corresponding to formula (I) where M is Zn.

Additionally or alternatively, the above listed linkers may be optionally, independently substituted at each carbon atom with substituents selected from the group consisting of alkyl, halo, cyano and nitro. Examples of alkyls include, but are not limited $C_1$-alkyl, $C_2$-alkyl, $C_3$-alkyl, $C_4$-alkyl, $C_5$-alkyl, $C_6$-alkyl, $C_7$-alkyl and $C_8$-alkyl. Ranges expressly disclosed include combinations of the above-enumerated values, e.g., $C_1$-$C_8$-alkyl, $C_1$-$C_6$-alkyl, $C_2$-$C_4$-alkyl, etc. Examples of halo substituents include, but are not limited to fluoro, chloro, bromo and/or iodo.

Additionally or alternatively, the ZIF material may comprise any one of the above-listed linkers and have any one of the above-listed framework types. For example, the ZIF material can include benzimidazole linkers corresponding to formula (I) with SOD framework. Additionally or alternatively, the ZIF material can include azabenzimadazole linkers corresponding to formula (II) with LTA framework.

Additionally or alternatively, the ZIF material can include azabenzimadazole linkers corresponding to formula (II) with SOD framework.

Additionally or alternatively, the adsorbent material can include one or more ZIF material, two or more ZIF materials, three or more ZIF materials, four or more ZIF materials or five or more ZIF materials, where the ZIF material can be the same or different. Additionally or alternatively, the adsorbent can include two or less ZIF materials, three or less ZIF materials, four or less ZIF materials or five or less ZIF materials, where the ZIF material can be the same or different. Ranges expressly disclosed include combinations of the above-enumerated upper and lower limits, e.g., one to five ZIF materials, two to four ZIF materials, three to five ZIF materials, etc.

Additionally or alternatively, the ZIF material may have selectivity for adsorbing organic compounds in a solution as measured by an adsorptive loading ratio. The solution may be aqueous or non-aqueous. Examples of non-aqueous solutions include, but are not limited to organic solvents, such as toluene, hexane, pentane, benzene, acetone, and alcohols. Examples of organic compounds include, but are not limited to alkanes, alkenes and alcohols. Examples of alkanes include, but are not limited to methane, ethane, propane, butane, pentane, hexane and octane. Examples of alkenes include, but are not limited to ethene, propene, butene, hexene and octene. Examples of alcohols include, but are not limited to methanol, ethanol, propanol and butanol (e.g., isobutanol, n-butanol, tert-butanol, 2-methyl-1-butanol, 3-methyl-2-butanol, etc.).

As understood in the art, an adsorptive loading ratio of a material for one component over another component, for example component A over component B, can be determined by separately measuring the uptake capacity of the material for component A and component B at similar temperatures. The adsorptive loading ratio for component A over component B=uptake capacity for component A/uptake capacity for component B.

For example, the ZIF material may independently have an adsorptive loading ratio for alcohols over water, such as, but not limited to methanol over water, ethanol over water, butanol (e.g., isobutanol, n-butanol, tert-butanol, 2-methyl-1-butanol, 3-methyl-2-butanol, etc.) over water and/or 1-pentanol over water of at least ~1.0, at least ~1.1, at least ~1.2, at least ~1.3, at least ~1.4, at least ~1.5, at least ~1.6, at least ~1.7, at least ~1.8, at least ~1.9, at least ~2, at least ~4, at least ~6, at least ~8, at least ~10, at least ~11, at least ~12, at least ~13, at least ~14, at least ~15, at least ~16, at least ~17, at least ~18, at least ~19, at least ~20, at least ~21, at least ~22, at least ~23, at least ~24, at least ~25, at least ~26, at least ~27, at least ~28, at least ~29, at least ~30, at least ~31, at least ~32, at least ~33, at least ~34, at least ~35, at least ~36, at least ~37, at least ~38, at least ~39, at least ~40, at least ~42, at least ~44, at least ~46, at least ~48, at least ~50, at least ~55, at least ~60, at least ~65, at least ~70, at least ~72, at least ~74, at least ~76, at least ~77, at least ~78, at least ~80, at least ~81, at least ~82, at least ~83, at least ~84, at least ~85, at least ~86, at least ~87, at least ~88, at least ~89, at least ~90, at least ~91, at least ~92, at least ~93, at least ~94, at least ~95, at least ~96, at least ~97, at least ~98, at least ~99, at least ~100, at least ~102, at least ~104, at least ~106, at least ~108, at least ~110, at least ~120, at least ~130, at least ~140, at least ~150, at least ~160, at least ~170, at least ~180, at least ~190, at least ~200, at least ~210, at least ~220, at least ~230, at least ~240, at least ~250, at least ~260, at least ~270, at least ~280, at least ~290, at least ~300, at least ~310, at least ~320, at least ~330, at least ~340, at least ~350, at least ~360, at least ~370, at least ~380, at least ~390, at least ~400, at least ~410, at least ~420, at least ~430, at least ~440, at least ~450, at least ~460, at least ~470, at least ~480, at least ~490, at least ~500, at least ~510, at least ~520, at least ~530, at least ~540, at least ~550, at least ~560, at least ~570, at least ~580, at least ~590, and at least ~600. Particularly, the ZIF material has an adsorptive loading ratio for methanol over water of at least ~1, at least ~10, at least ~18, at least ~20 or at least ~39. Particularly, the ZIF material has an adsorptive loading ratio for ethanol over water of at least ~1, at least ~25, at least ~30, at least ~38, at least ~85, at least ~90 or at least ~94. Particularly, the ZIF material has an adsorptive loading ratio for 1-pentanol over water of at least ~1, at least ~20 or at least ~30. Additionally or alternatively, the ZIF material has an adsorptive loading ratio for alcohols over water, such as, but not limited to methanol over water, ethanol over water, butanol (e.g., isobutanol, n-butanol, tert-butanol, 2-methyl-1-butanol, 3-methyl-2-butanol, etc.) over water and/or 1-pentanol over water of less than ~1.0, less than ~1.1, less than ~1.2, less than ~1.3, less than ~1.4, less than ~1.5, less than ~1.6, less than ~1.7, less than ~1.8, less than ~1.9, less than ~2, less than ~4, less than ~6, less than ~8, less than ~10, less than ~11, less than ~12, less than ~13, less than ~14, less than ~15, less than ~16, less than ~17, less than ~18, less than ~19, less than ~20, less than ~21, less than ~22, less than ~23, less than ~24, less than ~25, less than ~26, less than ~27, less than ~28, less than ~29, less than ~30, less than ~31, less than ~32, less than ~33, less than ~34, less than ~35, less than ~36, less than ~37 less than ~38, less than ~39, less than ~40, less than ~42, less than ~44, less than ~46, less than ~48, less than ~50, less than ~55, less than ~60, less than ~65, less than ~70, less than ~72, less than ~74, less than ~76, less than ~77, less than ~78, less than ~80, less than ~81, less than ~82, less than ~83, less than ~84, less than ~85, less than ~86, less than ~87, less than ~88, less than ~89, less than ~90, less than ~91, less than ~92, less than ~93, less than ~94, less than ~95, less than ~96, less than ~97, less than ~98, less than ~99, less than ~100, less than ~102, less than ~104, less than ~106, less than ~108, less than ~110, less than ~120, less than ~130, less than ~140, less than ~150, less than ~160, less than ~170, less than ~180, less than ~190, less than ~200, less than ~210, less than ~220, less than ~230, less than ~240, less than ~250, less than ~260, less than ~270, less than ~280, less than ~290, less than ~300, less than ~310, less than ~320, less than ~330, less than ~340, less than ~350, less than ~360, less than ~370, less than ~380, less than ~390, less than ~400, less than ~410, less than ~420, less than ~430, less than ~440, less than ~450, less than ~460, less than ~470, less than ~480, less than ~490, less than ~500, less than ~510, less than ~520, less than ~530, less than ~540, less than ~550, less than ~560, less than ~570, less than ~580, less than ~590, and less than ~600. Ranges expressly disclosed include combinations of the above-enumerated upper and lower limits, e.g., ~1.0 to ~600, ~1.1 to ~500, ~4 to ~50, ~10 to ~42, ~20 to ~40, ~33 to ~46, etc.

The ZIF material's adsorptive loading ratios as described above may occur at a temperature of at least ~5° C., at least ~10° C., at least ~15° C., at least ~20° C., at least ~25° C., at least ~30° C., at least ~35° C., at least ~40° C., at least ~45° C., at least ~50° C., at least ~55° C., at least ~60° C., at least ~65° C., at least ~70° C., at least ~75° C., at least ~80° C., at least ~85° C., at least ~90° C., at least ~95° C., at least ~100° C., at least ~105° C., and at least ~110° C. Additionally or alternatively, the ZIF material's adsorptive loading ratios as described above may occur at a temperature of less than ~5° C., less than ~10° C., less than ~15° C., less than ~20° C., less than ~25° C., less than ~30° C., less than ~35° C., less than ~40° C., less than ~45° C., less than ~50° C., less than ~55° C., less than ~60° C., less than ~65° C., less than ~70° C., less than ~75° C., less than ~80° C., less than ~85° C., less than ~90° C., less than ~95° C., less than ~100° C., less than ~105° C., and less than ~110° C. Ranges expressly disclosed include combinations of the above-enumerated upper and lower limits, e.g., 5° C. to ~110° C., ~20° C. to ~50° C., ~30° C. to ~75° C., ~60° C. to ~95° C., etc.

Particularly, the ZIF material has an adsorptive loading ratio of at least ~1 at ~10° C. to ~95° C. for: (i) for methanol over water; (ii) ethanol over water; and/or (iii) for 1-pentanol over water.

Additionally or alternatively, the ZIF material has the following adsorptive loading ratios: (i) for methanol over water at ~10° C. to ~50° C. (e.g., ~30° C.) of at least ~20 or at least ~39; (ii) for methanol over water at ~55° C. to ~95° C. (e.g., ~75° C.) of at least ~10 or at least ~18; (iii) for ethanol over water at ~10° C. to ~50° C. (e.g., ~30° C.) of at least ~25, at least ~30 or at least ~38; (iv) for ethanol over water at ~55° C. to ~95° C. (e.g., ~75° C.) of at least ~85, at least ~90 or at least ~94; and/or (v) for 1-pentanol over water at ~10° C. to ~50° C. (e.g., ~30° C.) of at least ~20 or at least ~30.

Additionally or alternatively, the ZIF material is capable of lowering the concentration of organic compounds as described above in aqueous or non-aqueous solutions. For example, the ZIF material is capable of lowering the concentration of alcohols, such as but not limited to methanol, ethanol, propanol, butanol (e.g., isobutanol, n-butanol, tert-butanol, 2-methyl-1-butanol, 3-methyl-2-butanol, etc.) and mixtures thereof, in water to less than or equal to ~20.0 wt. %, less than or equal to ~19.0 wt. %, less than or equal to ~18.0 wt. %, less than or equal to ~17.0 wt. %, less than or equal to ~16.0 wt. %, less than or equal to ~15.0 wt. %, less than or equal to ~14.0 wt. %, less than or equal to ~13.0 wt. %, less than or equal to ~12.0 wt. %, less than or equal to ~11.0 wt. %, less than or equal to ~10.0 wt. %, less than or equal to ~9.0 wt. %, less than or equal to ~8.0 wt. %, less than or equal to ~7.0 wt. %, less than or equal to ~6.0 wt. %, less than or equal to ~5.0 wt. %, less than or equal to ~4.0 wt. %, less than or equal to ~3.0 wt. %, less than or equal to ~2.0 wt. %, less than or equal to ~1.8 wt. %, less than or equal to ~1.6 wt. %, less than or equal to ~1.4 wt. %, less than or equal to ~1.2 wt. %, less than or equal to ~1.0 wt. %, less than or equal to ~0.9 wt. %, less than or equal to ~0.8 wt. %, less than or equal to ~0.7 wt. %, less than or equal to ~0.6 wt. %, less than or equal to ~0.5 wt. %, less than or equal to ~0.4 wt. %, less than or equal to ~0.3 wt. %, less than or equal to ~0.2 wt. %, less than or equal to ~0.1 wt. %, less than or equal to ~0.09 wt. %, less than or equal to ~0.08 wt. %, less than or equal to ~0.07 wt. %, less than or equal to ~0.06 wt. %, less than or equal to ~0.05 wt. %, less than or equal to ~0.04 wt. %, less than or equal to ~0.03 wt. %, less than or equal to ~0.02 wt. %, less than or equal to ~0.01 wt. %, less than or equal to ~0.009 wt. %, less than or equal to ~0.008 wt. %, less than or equal to ~0.007 wt. %, less than or equal to ~0.006 wt. %, less than or equal to ~0.005 wt. %, less than or equal to ~0.004 wt. %, less than or equal to ~0.003 wt. %, less than or equal to ~0.002 wt. % and less than or equal to ~0.001 wt. %. Particularly, the ZIF material is capable of lowering the concentration of ethanol in water to less than or equal to ~0.9 wt. %, less than or equal to ~0.3 wt. %, less than or equal to ~0.2 wt. % or less than or equal to ~0.001 wt. %. Ranges expressly disclosed include combinations of the above-enumerated values, e.g., 0.001 wt. % to ~20.0 wt. %, ~0.01 wt. % to ~5.0 wt. %, ~0.1 wt. % to ~2.0 wt. %, ~0.2 wt. % to ~1.6 wt. %, ~0.4 wt. % to ~1.8 wt. %, etc.

Additionally or alternatively, the ZIF material is capable of lowering the concentration of organic compounds, such alkanes and alkenes, in non-aqueous solutions, such as toluene. For example, the ZIF material is capable of lowering the concentration of hexane and/or hexene in toluene to less than or equal to ~1.5 wt. %, less than or equal to ~1.4 wt. %, less than or equal to ~1.3 wt. %, less than or equal to ~1.2 wt. %, less than or equal to ~1.1 wt. %, less than or equal to ~1.0 wt. %, less than or equal to ~0.9 wt. %, less than or equal to ~0.8 wt. %, less than or equal to ~0.7 wt. %, less than or equal to ~0.6 wt. %, less than or equal to ~0.5 wt. %, less than or equal to ~0.4 wt. %, less than or equal to ~0.3 wt. %, less than or equal to ~0.2 wt. %, less than or equal to ~0.1 wt. %, less than or equal to ~0.09 wt. %, less than or equal to ~0.08/wt. %, less than or equal to ~0.07 wt. %, less than or equal to ~0.06 wt. %, less than or equal to ~0.05 wt. %, less than or equal to ~0.03 wt. %, less than or equal to ~0.02 wt. % and less than or equal to ~0.01 wt. %. Particularly, the ZIF material is capable of lowering the concentration of hexane and/or hexene in toluene to less than or equal to ~0.1 wt. %. Ranges expressly disclosed include combinations of the above-enumerated values, e.g., ~0.01 wt. % to ~1.5 wt. %, ~0.06 wt. % to ~1.1 wt. %, ~0.02 wt. % to ~0.07 wt. %, etc.

B. Cross-Linked Polymer

The adsorbent material also comprises a cross-linked polymer. The cross-linked polymer comprises multiple monomers containing a moiety corresponding in structure to Formula (I):

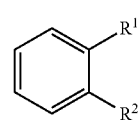

wherein $R^1$ and $R^2$ are independently selected from the group consisting of hydrogen, alkyl, alkenyl aryl, $C(R^3)_3$ in which each $R^3$ is independently hydrogen or aryl; or, taken together, $R^1$ and $R^2$ form a monocyclic or polycyclic aromatic hydrocarbon.

Additionally or alternatively, the alkyl is a $C_1$-alkyl, $C_2$-alkyl, $C_3$-alkyl, $C_4$-alkyl, $C_5$-alkyl, $C_6$-alkyl, $C_6$-alkyl, $C_7$-alkyl or $C_8$-alkyl. Ranges expressly disclosed include combinations of the above-enumerated values, e.g., $C_1$-$C_8$-alkyl, $C_1$-$C_6$-alkyl, $C_1$-$C_3$-alkyl, $C_2$-$C_4$-alkyl, etc. In particular, the alkyl is a $C_1$-$C_6$-alkyl, $C_1$-$C_3$-alkyl or $C_1$-$C_2$-alkyl.

Additionally or alternatively, the alkenyl is a $C_2$-alkenyl, $C_3$-alkenyl, $C_4$-alkenyl, $C_5$-alkenyl, $C_6$-alkenyl, $C_7$-alkenyl or $C_8$-alkenyl. Ranges expressly disclosed include combinations of the above-enumerated values, e.g., $C_2$-$C_8$-alkenyl, $C_2$-$C_6$-alkenyl, $C_2$-$C_3$-alkenyl, $C_2$-$C_4$-alkenyl, etc. In particular, the alkenyl is a $C_2$-$C_6$-alkenyl, $C_2$-$C_4$-alkenyl or $C_2$-$C_3$-alkenyl.

Additionally or alternatively, the aryl contains 6 to 14 carbon ring atoms. Exemplary aryls include, but are not limited to phenyl, naphthyl, indolyl, tolyl and xylyl. Particularly, the aryl is selected from the group consisting of phenyl, naphthyl and indolyl, in particular, phenyl.

Additionally or alternatively, the monocyclic aromatic hydrocarbon can contain 4 or 6 carbon ring atoms, particularly 6 carbon ring atoms. Additionally or alternatively, the polycyclic aromatic hydrocarbon is bicyclic, tricyclic, tetracyclic or pentacyclic, particularly, tricyclic. The polycyclic aromatic hydrocarbon can comprise at least one aromatic hydrocarbon ring, such as benzene, attached to either another aromatic ring or a non-aromatic ring, such as a cycloalkyl, in a fused, pendant or bridged manner, particularly in a bridged manner. The cycloalkyl can contain 4-10 carbon ring atoms, particularly 8-carbon ring atoms. An example of a polycyclic aromatic hydrocarbon is two benzene rings fused to a bridged eight-membered cycloalkyl.

In one embodiment, $R^1$ and $R^2$ are independently selected from the group consisting of hydrogen, $C_1$-$C_6$-alkyl, aryl, $C(R^3)_3$ in which each $R^3$ is independently hydrogen or aryl; or, taken together, $R^1$ and $R^2$ form a monocyclic or polycyclic aromatic hydrocarbon. Additionally or alternatively, $R^1$ and $R^2$ are independently selected from the group consisting of hydrogen; $C_1$-$C_3$-alkyl; an aryl selected from the group consisting of phenyl, naphthyl and indolyl; $C(R^3)_3$ in which each $R^3$ is independently hydrogen or aryl selected from the group consisting of phenyl, naphthyl and indolyl; or, taken together, $R^1$ and $R^2$ form a monocyclic, bicyclic or tricyclic aromatic hydrocarbon. Additionally or alternatively, $R^1$ and $R^2$ are independently selected from the group consisting of hydrogen; $C_1$-$C_2$-alkyl; phenyl; $C(R^3)_3$ in which each $R^3$ is independently hydrogen or phenyl; or, taken together, $R^1$ and $R^2$ form a monocyclic or tricyclic aromatic hydrocarbon.

In another embodiment, the cross-linked polymer comprises multiple monomers containing a moiety selected from the group consisting of the following moieties:

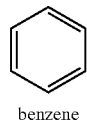

(a)

benzene

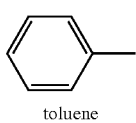

(b)

toluene

(c)

ethyl benzene

(d)

naphthalene

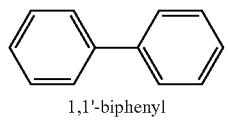

(e)

1,1'-biphenyl

-continued

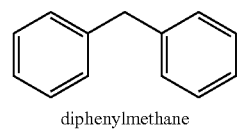

(f)

diphenylmethane

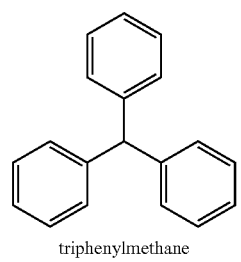

(g)

triphenylmethane

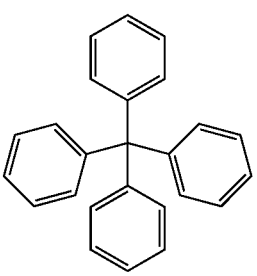

(e)

tetraphenylmethane (f)

triptycene

Particularly, the cross-linked polymer comprises multiple monomers containing benzene.

The cross-linked polymer can be prepared according to the Friedel-Crafts alkylation of the monomers as described by Woodward, R. et al. *J. Am. Chem. Soc.*, 136: 9028–9035 (2014), the entirety of which is herein incorporated by reference. The cross-linkers in the cross-linked polymer independently may be a $C_1$-$C_8$-alkyl. In particular, the cross-linked polymer may comprise multiple benzene monomers and correspond to the following structure:

(1)

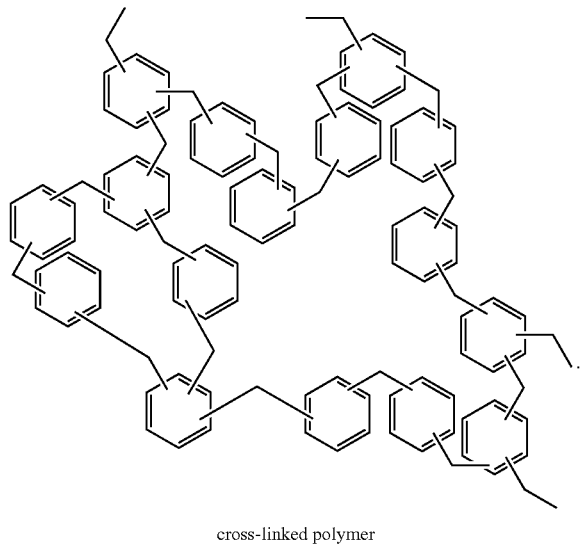

cross-linked polymer

Additionally or alternatively, the cross-linked polymer may have selectivity for adsorbing organic compounds in a solution as described above, as measured by an adsorptive loading ratio. For example, the cross-linked polymer has an adsorptive loading ratio for butanol (e.g., isobutanol, n-butanol, tert-butanol) over water of at least ~0.1, at least ~0.2, at least ~0.4, at least ~0.6, at least ~0.8, at least ~1.0, at least ~1.1, at least ~1.2, at least ~1.3, at least ~1.4, at least ~1.5, at least ~1.6, at least ~1.7, at least ~1.8, at least ~1.9, at least ~2.0, at least ~2.2, at least ~2.4, at least ~2.6, at least ~2.8, at least ~3.0, at least ~3.2, at least ~3.4, at least ~3.6, at least ~3.8, at least ~4, at least ~6, at least ~8, at least ~10, at least ~11, at least ~12, at least ~13, at least ~14, at least ~15, at least ~16, at least ~17, at least ~18, at least ~19, at least ~20, at least ~21, at least ~22, at least ~23, at least ~24, at least ~25, at least ~26, at least ~27, at least ~28, at least ~29, at least ~30, at least ~31, at least ~32, at least ~33, at least ~34, at least ~35, at least ~36, at least ~37, at least ~38, at least ~39, at least ~40, at least ~42, at least ~44, at least ~46, at least ~48, at least ~50, at least ~55, at least ~60, at least ~65, at least ~70, at least ~72, at least ~74, at least ~76, at least ~77, at least ~78, at least ~80, at least ~81, at least ~82, at least ~83, at least ~84, at least ~85, at least ~86, at least ~87, at least ~88, at least ~89, at least ~90, at least ~91, at least ~92, at least ~93, at least ~94, at least ~95, at least ~96, at least ~97, at least ~98, at least ~99, at least ~100, at least ~102, at least ~104, at least ~106, at least ~108, at least ~110, at least ~120, at least ~130, at least ~140, at least ~150, at least ~160, at least ~170, at least ~180, at least ~190, at least ~200, at least ~210, at least ~220, at least ~230, at least ~240, at least ~250, at least ~260, at least ~270, at least ~280, at least ~290, at least ~300, at least ~310, at least ~320, at least ~330, at least ~340, at least ~350, at least ~360, at least ~370, at least ~380, at least ~390, at least ~400, at least ~410, at least ~420, at least ~430, at least ~440, at least ~450, at least ~460, at least ~470, at least ~480, at least ~490, at least ~500, at least ~510, at least ~520, at least ~530, at least ~540, at least ~550, at least ~560, at least ~570, at least ~580, at least ~590, and at least ~600. Particularly, the cross-linked polymer has an adsorptive loading ratio for isobutanol over water of at least ~1.0, at least ~1.5, or at least ~10. Additionally or alternatively, the cross-linked polymer has an adsorptive loading ratio for butanol (e.g., isobutanol, n-butanol, tert-butanol) over water at of less than ~0.1, less than ~0.2, less than ~0.4, less than ~0.6, less than ~0.8, less than ~1.0, less than ~1.1, less than ~1.2, less than ~1.3, less than ~1.4, less than ~1.5, less than ~1.6, less than ~1.7, less than ~1.8, less than ~1.9, less than ~2.0, less than ~2.2, less than ~2.4, less than ~2.6, less than ~2.8, less than ~3.0, less than ~3.2, less than ~3.4, less than ~3.6, less than ~3.8, less than ~4, less than ~6, less than ~8, less than ~10, less than ~11, less than ~12, less than ~13, less than ~14, less than ~15, less than ~16, less than ~17, less than ~18, less than ~19, less than ~20, less than ~21, less than ~22, less than ~23, less than ~24, less than ~25, less than ~26, less than ~27, less than ~28, less than ~29, less than ~30, less than ~31, less than ~32, less than ~33, less than ~34, less than ~35, less than ~36, less than ~37 less than ~38, less than ~39, less than ~40, less than ~42, less than ~44, less than ~46, less than ~48, less than ~50, less than ~55, less than ~60, less than ~65, less than ~70, less than ~72, less than ~74, less than ~76, less than ~77, less than ~78, less than ~80, less than ~81, less than ~82, less than ~83, less than ~84, less than ~85, less than ~86, less than ~87, less than ~88, less than ~89, less than ~90, less than ~91, less than ~92, less than ~93, less than ~94, less than ~95, less than ~96, less than ~97, less than ~98, less than ~99, less than ~100, less than ~102, less than ~104, less than ~106, less than ~108, less than ~110, less than ~120, less than ~130, less than ~140, less than ~150, less than ~160, less than ~170, less than ~180, less than ~190, less than ~200, less than ~210, less than ~220, less than ~230, less than ~240, less than ~250, less than ~260, less than ~270, less than ~280, less than ~290, less than ~300, less than ~310, less than ~320, less than ~330, less than ~340, less than ~350, less than ~360, less than ~370, less than ~380, less than ~390, less than ~400, less than ~410, less than ~420, less than ~430, less than ~440, less than ~450, less than ~460, less than ~470, less than ~480, less than ~490, less than ~500, less than ~510, less than ~520, less than ~530, less than ~540, less than ~550, less than ~560, less than ~570, less than ~580, less than ~590, and less than ~600. Ranges expressly disclosed include combinations of the above-enumerated upper and lower limits, e.g., ~0.1 to ~600, ~1.2 to ~240, ~0.8 to ~1.5, ~90 to ~310, etc.

The cross-linked polymer's adsorptive loading ratios as described above may occur at a temperature of at least ~5° C., at least ~10° C., at least ~15° C., at least ~20° C., at least ~25° C., at least ~30° C., at least ~35° C., at least ~40° C., at least ~45° C., at least ~50° C., at least ~55° C., at least ~60° C., at least ~65° C., at least ~70° C., at least ~75° C., at least ~80° C., at least ~85° C., at least ~90° C., at least ~95° C., at least ~100° C., at least ~105° C., and at least ~110° C. Additionally or alternatively, the cross-linked polymer's adsorptive loading ratios as described above may occur at a temperature of less than ~5° C., less than ~10° C., less than ~15° C., less than ~20° C., less than ~25° C., less than ~30° C., less than ~35° C., less than ~40° C., less than ~45° C., less than ~50° C., less than ~55° C., less than ~60° C., less than ~65° C., less than ~70° C., less than ~75° C., less than ~80° C., less than ~85° C., less than ~90° C., less than ~95° C., less than ~100° C., less than ~105° C., and less than ~110° C. Ranges expressly disclosed include combinations of the above-enumerated upper and lower limits, e.g., ~5° C. to ~110° C., ~20° C. to ~50° C., ~30° C. to ~75° C., ~60° C. to ~95° C., etc. Particularly, the cross-linked polymer has an adsorptive loading ratio for isobutanol over water at ~10° C. to ~50° C. (e.g., ~30° C.) of at least ~1.0 or at least ~1.5.

Additionally or alternatively, the cross-linked polymer is capable of lowering the concentration of organic compounds as described above in aqueous or non-aqueous solutions as described above. For example, the cross-linked polymer is capable of lowering the concentration of butanol (e.g., isobutanol, n-butanol, tert-butanol) in water to less than or equal to ~10.0 wt. %, less than or equal to ~9.0 wt. %, less than or equal to ~8.0 wt. %, less than or equal to ~7.0 wt. %, less than or equal to ~6.0 wt. %, less than or equal to ~5.0 wt. %, less than or equal to ~4.0 wt. %, less than or equal to ~3.0 wt. %, less than or equal to ~2.0 wt. %, less than or equal to ~1.0 wt. %, less than or equal to ~0.9 wt. %, less than or equal to ~0.8 wt. %, less than or equal to ~0.7 wt. %, less than or equal to ~0.6 wt. %, less than or equal to ~0.5 wt. %, less than or equal to ~0.4 wt. %, less than or equal to ~0.3 wt. %, less than or equal to ~0.2 wt. %, less than or equal to ~0.1 wt. %, less than or equal to ~0.09 wt. %, less than or equal to ~0.08 wt. %, less than or equal to ~0.07 wt. %, less than or equal to ~0.06 wt. %, less than or equal to ~0.05 wt. %, less than or equal to ~0.04 wt. %, less than or equal to ~0.03 wt. %, less than or equal to ~0.02 wt. %, less than or equal to ~0.01 wt. %, less than or equal to ~0.009 wt. %, less than or equal to ~0.008 wt. %, less than or equal to ~0.007 wt. %, less than or equal to ~0.006 wt. %, less than or equal to ~0.005 wt. %, less than or equal to ~0.004 wt. %, less than or equal to ~0.003 wt. %, less than or equal to ~0.002 wt. % and less than or equal to ~0.001 wt. %. Particularly, the cross-linked polymer is capable of lowering the concentration of butanol (e.g., isobutanol, n-butanol, tert-butanol) in water to less than or equal to ~0.9 wt. %, less than or equal to ~0.1 wt. % or less than or equal to ~0.02 wt. % or less than or equal to ~0.001 wt. %. Ranges expressly disclosed include combinations of the above-enumerated values, e.g., 0.001 wt. % to ~10.0 wt. %, ~0.008 wt. % to ~5.0 wt. %, ~0.01 wt. % to ~1.0 wt. %, ~0.03 wt. % to ~0.8 wt. %, ~0.02 wt. % to ~0.9 wt. %, etc.

Additionally or alternatively, the adsorbent material can include one or more cross-linked polymers, two or more cross-linked polymers, three or more cross-linked polymers, four or more cross-linked polymers or five or more cross-linked polymers, where the cross-linked polymers are the same or different. Additionally or alternatively, the adsorbent can include two or less cross-linked polymers, three or less cross-linked polymers, four or less cross-linked polymers or five or less cross-linked polymers, where the cross-linked polymers are the same or different. Ranges expressly disclosed include combinations of the above-enumerated upper and lower limits, e.g., one to five cross-linked polymers, two to four cross-linked polymers, three to five cross-linked polymers, etc.

In various aspects, an adsorbent material is provided comprising a ZIF material having:
(i) an adsorptive loading ratio for methanol over water of at least ~1 at ~10° C. to ~95° C.;
(ii) an adsorptive loading ratio for ethanol over water of at least ~1 at ~10° C. to ~95° C.; and/or
(iii) an adsorptive loading ratio for 1-pentanol over water of at least ~1 at ~10° C. to ~95° C.; and
a cross-linked polymer having an adsorptive loading ratio for isobutanol over water of at least ~1 at ~10° C. to ~50° C. The ZIF material and cross-linked polymer are as described above.

In various aspects, an adsorbent material is provided comprising a ZIF material having:
(iv) an adsorptive loading ratio for methanol over water of at least ~20 at ~10° C. to ~50° C. and at least ~10 at ~55° C. to ~95° C.;
(v) an adsorptive loading ratio for ethanol over water of at least ~25 at ~10° C. to ~50° C. and at least ~85 at ~55° C. to ~95° C.; and/or
(vi) an adsorptive loading ratio for 1-pentanol over water of at least ~20 at ~10° C. to ~50° C.; and
a cross-linked polymer having an adsorptive loading ratio for isobutanol over water of at least ~1 at ~10° C. to ~50° C. Particularly, the ZIF material has an adsorptive loading ratio for ethanol over water of at least 30 at 30° C. and at least 90 at 75° C. The ZIF material and cross-linked polymer are as described above.

III. Methods of Separating Organic Compounds

In various aspects, a method for separating at least one organic compound from a solution is provided herein. The method comprises contacting the solution with an adsorbent material as described herein.

Additionally or alternatively, the at least one organic compound is present in the solution in a concentration of greater than or equal to ~0.001 wt. %, greater than or equal to ~0.002 wt. %, greater than or equal to ~0.003 wt. %, greater than or equal to ~0.004 wt. %, greater than or equal to ~0.005 wt. %, greater than or equal to ~0.006 wt. %, greater than or equal to ~0.007 wt. %, greater than or equal to ~0.008 wt. %, greater than or equal to ~0.009 wt. %, greater than or equal to ~0.01 wt. %, greater than or equal to ~0.02 wt. %, greater than or equal to ~0.03 wt. %, greater than or equal to ~0.04 wt. %, greater than or equal to ~0.05 wt. %, greater than or equal to ~0.06 wt. %, greater than or equal to ~0.07 wt. %, greater than or equal to ~0.08 wt. %, greater than or equal to ~0.09 wt. %, greater than or equal to ~0.1 wt. %, greater than or equal to ~0.2 wt. %, greater than or equal to ~0.3 wt. %, greater than or equal to 0.4 wt. %, greater than or equal to ~0.5 wt. %, greater than or equal to ~0.6 wt. %, greater than or equal to ~0.7 wt. %, greater than or equal to ~0.8 wt. %, greater than or equal to ~0.9 wt. %, greater than or equal to ~1.0 wt. %, greater than or equal to ~2.0 wt. %, greater than or equal to ~3.0 wt. %, greater than or equal to ~4.0 wt. %, greater than or equal to ~5.0 wt. %, greater than or equal to ~6.0 wt. %, greater than or equal to ~7.0 wt. %, greater than or equal to ~8.0 wt. %, greater than or equal to 9.0 wt. %, greater than or equal to ~10.0 wt. %, greater than or equal to ~12.0 wt. %, greater than or equal to ~14.0 wt. %, greater than or equal to ~16.0 wt. %, greater than or equal to ~18.0 wt. % and greater than or equal to ~20.0 wt. %. Particularly, the at least one organic compound is present in the solution in a concentration of greater than or equal to ~0.02 wt. % or greater than or equal to ~0.5 wt. %. Additionally or alternatively, the at least one organic compound is present in the solution in a concentration of less than or equal to ~0.001 wt. %, less than or equal to ~0.002 wt. %, less than or equal to ~0.003 wt. %, less than or equal to ~0.004 wt. %, less than or equal to ~0.005 wt. %, less than or equal to ~0.006 wt. %, less than or equal to ~0.007 wt. %, less than or equal to ~0.008 wt. %, less than or equal to ~0.009 wt. %, less than or equal to ~0.01 wt. %, less than or equal to ~0.02 wt. %, less than or equal to ~0.03 wt. %, less than or equal to ~0.04 wt. %, less than or equal to ~0.05 wt. %, less than or equal to ~0.06 wt. %, less than or equal to ~0.07 wt. %, less than or equal to ~0.08 wt. %, less than or equal to ~0.09 wt. %, less than or equal to ~0.1 wt. %, less than or equal to ~0.2 wt. %, less than or equal to ~0.3 wt. %, less than or equal to 0.4 wt. %, less than or equal to ~0.5 wt.

%, less than or equal to ~0.6 wt. %, less than or equal to ~0.7 wt. %, less than or equal to ~0.8 wt. %, less than or equal to ~0.9 wt. %, less than or equal to ~1.0 wt. %, less than or equal to ~2.0 wt. %, less than or equal to ~3.0 wt. %, less than or equal to ~4.0 wt. %, less than or equal to ~5.0 wt. %, less than or equal to ~6.0 wt. %, less than or equal to ~7.0 wt. %, less than or equal to ~8.0 wt. %, less than or equal to 9.0 wt. %, less than or equal to ~10.0 wt. %, less than or equal to ~12.0 wt. %, less than or equal to ~14.0 wt. % less than or equal to ~16.0 wt. %, less than or equal to ~18.0 wt. % and less than or equal to ~20.0 wt. %. Particularly, the at least one organic compound is present in the solution in a concentration of less than or equal to ~10.0 wt. % or less than or equal to ~5.0 wt. %. Ranges expressly disclosed include combinations of the above-enumerated upper and lower limits, e.g., 0.001 wt. % to ~20.0 wt. %, ~0.01 wt. % to ~16.0 wt. %, ~0.02 wt. % to ~10.0 wt. %, ~0.1 wt. % to ~6.0 wt. %, etc. Particularly, the at least one organic compound is present in the solution in a concentration of ~0.02 wt. % to ~10.0 wt. % or ~0.5 wt. % to ~5 wt. %.

Additionally or alternatively, the adsorbent material is present in amount capable of lowering the concentration of the at least one organic compound in the solution to less than or equal to ~20.0 wt. %, less than or equal to ~19.0 wt. %, less than or equal to ~18.0 wt. %, less than or equal to ~17.0 wt. %, less than or equal to ~16.0 wt. %, less than or equal to ~15.0 wt. %, less than or equal to ~14.0 wt. %, less than or equal to ~13.0 wt. %, less than or equal to ~12.0 wt. %, less than or equal to ~11.0 wt. %, less than or equal to ~10.0 wt. %, less than or equal to ~9.0 wt. %, less than or equal to ~8.0 wt. %, less than or equal to ~7.0 wt. %, less than or equal to ~6.0 wt. %, less than or equal to ~5.0 wt. %, less than or equal to ~4.0 wt. %, less than or equal to ~3.0 wt. %, less than or equal to ~2.0 wt. %, less than or equal to ~1.9 wt. %, less than or equal to ~1.8 wt. %, less than or equal to ~1.8 wt. %, less than or equal to ~1.7 wt. %, less than or equal to ~1.6 wt. %, less than or equal to ~1.5 wt. %, less than or equal to ~1.4 wt. %, less than or equal to ~1.3 wt. %, less than or equal to ~1.2 wt. %, less than or equal to ~1.1 wt. %, less than or equal to ~1.0 wt. %, less than or equal to ~0.9 wt. %, less than or equal to ~0.8 wt. %, less than or equal to ~0.7 wt. %, less than or equal to ~0.6 wt. %, less than or equal to ~0.5 wt. %, less than or equal to ~0.4 wt. %, less than or equal to ~0.3 wt. %, less than or equal to ~0.2 wt. %, less than or equal to ~0.1 wt. %, less than or equal to ~0.09 wt. %, less than or equal to ~0.08 wt. %, less than or equal to ~0.07 wt. %, less than or equal to ~0.06 wt. %, less than or equal to ~0.05 wt. %, less than or equal to ~0.03 wt. %, less than or equal to ~0.02 wt. % and less than or equal to ~0.01 wt. %, less than or equal to ~0.009 wt. %, less than or equal to ~0.008 wt. %, less than or equal to ~0.007 wt. %, less than or equal to ~0.006 wt. %, less than or equal to ~0.005 wt. %, less than or equal to ~0.004 wt. %, less than or equal to ~0.003 wt. %, less than or equal to ~0.002 wt. % and less than or equal to ~0.001 wt. %. Particularly, the adsorbent material is present in an amount capable of lowering the concentration of the at least one organic compound in the solution to less than or equal to ~0.9 wt. % or less than or equal to ~0.3 wt. %. or less than or equal to ~0.001 wt. %. Ranges expressly disclosed include combinations of the above-enumerated values, e.g., 0.001 wt. % to ~20.0 wt. %, ~2.0 wt. % to ~16.0 wt. %, ~0.01 wt. % to ~1.5 wt. %, ~0.06 wt. % to ~1.1 wt. %, ~0.02 wt. % to ~0.07 wt. %, etc.

Additionally or alternatively, the adsorbent material is capable of separating 1, 2, 3, 4, 5, 6, 7, 8, 9, 10 or more organic compounds, where the organic compounds can be the same or different. Ranges expressly disclosed include combinations of the above-enumerated values, e.g., 1-10 organic compounds, 2-4 organic compounds, 3-6 organic compounds, etc.

Examples of organic compounds are described above.

The solution may be aqueous or non-aqueous. Examples of non-aqueous solutions are described above.

Additionally or alternatively, the adsorbent material, particularly the ZIF material and the cross-linked polymer are each present in amounts capable of lowering the concentration of ethanol and butanol as described above.

Additionally or alternatively, the method further comprises regenerating the adsorbent material once it becomes saturated with at least one organic compound, so that the adsorbent material can be re-used. As discussed herein, regenerating the adsorbent material refers to heating the ZIF material and cross-linked polymer either separately or together. For example, the adsorbent material may be heated to a temperature of at least about ~60° C., at least about ~70° C., at least about ~80° C., at least about ~90° C., at least about ~100° C., at least about ~110° C., at least about ~120° C., at least about ~130° C., at least about ~140° C., at least about ~150° C., at least about ~160° C., at least about ~170° C., at least about ~180° C., at least about ~190° C. or at least about ~200° C. Ranges expressly disclosed include combinations of the above-enumerated values, e.g., ~60° C. to ~200° C., ~120° C. to ~150° C., ~80° C. to ~100° C., etc. The heating may occur for at least about ~1 minute, at least about ~2 minutes, at least about ~4 minutes, at least about ~6 minutes at least, at least about ~8 minutes, at least about ~10 minutes, at least about ~12 minutes, about ~14 minutes, at least about ~16 minutes, at least about ~18 minutes, at least about ~20 minutes, at least about ~30 minutes, at least about ~40 minutes, at least about ~50 minutes, at least about ~60 minutes (~1 hour), at least about ~70 minutes, at least about ~80 minutes, at least about ~90 minutes, at least about ~100 minutes, at least about ~110 minutes or at least about ~120 minutes (~2 hours). Ranges expressly disclosed include combinations of the above-enumerated values, e.g., ~30 minutes to ~120 minutes, ~30 minutes to ~60 minutes, etc. In particular, the ZIF material may be heated to at least about ~150° C. for at least about ~30 minutes or at least about ~60 minutes or to at least about ~100° C. for at least about ~30 minutes. In particular, the cross-linked polymer may be heated to at least about ~100° C. for at least about ~30 minutes or at least about ~60 minutes, at least about ~80° C. for at least about ~60 minutes or at least about ~60° C. for at least about ~60 minutes.

IV. Biofuel Production Methods

In various aspects, a method of producing biofuel is provided herein. The method comprises hydrolyzing a biomass to form sugars, fermenting the sugars to produce an aqueous solution comprising one or more alcohols and separating the one or more alcohols from the aqueous solution with an adsorbent material as described herein.

Generally, biofuel can be produced by providing a biomass (e.g., corn, sugar cane, grass) and subjecting the biomass to hydrolytic action of enzymes which break down at least some of the complex starches or sugars into fermentable sugars, e.g. pentose. The fermentable sugars are transferred to fermenters where yeast can be added and the conversion of the fermentable sugars to one or more alcohols (e.g., methanol, ethanol, propanol, butanol) can occur. The one or more alcohols are typically present in large quantities of water and separation of the one or more alcohols from water is required.

Thus, the resultant aqueous solution of one or more alcohols can be passed through one or more packed beds containing the adsorbent material described herein thereby separating the one or more alcohols from the water. The packed bed of adsorbent material can be switched out once it becomes fully saturated with one or more alcohols. The saturated packed bed of adsorbent material can then be regenerated as described above.

Additionally or alternatively, the adsorbent material can be incorporated into a membrane which is used to separate the aqueous solution of one or more alcohols.

V. Further Embodiments

The invention can additionally or alternately include one or more of the following embodiments.

Embodiment 1

An adsorbent material comprising: a zeolitic imidazolate framework (ZIF) material comprising linkers selected from the group consisting of an optionally substituted benzimidazole linker, an optionally substituted azabenzimidazole linker, an optionally substituted purine linker, and any combination thereof; and a cross-linked polymer comprising multiple monomers containing a moiety corresponding in structure to Formula (I):

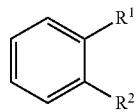

(I)

wherein $R^1$ and $R^2$ are independently selected from the group consisting of hydrogen, $C_1$-$C_6$-alkyl, aryl, $C(R^3)_3$ in which each $R^3$ is independently hydrogen or aryl; or, taken together, $R^1$ and $R^2$ form a monocyclic or polycyclic aromatic hydrocarbon, wherein the ZIF material optionally has (i) an adsorptive loading ratio for methanol over water of at least about 1 at about 10° C. to about 95° C.; (ii) an adsorptive loading ratio for ethanol over water of at least about 1 or at least about 20 at about at about 10° C. to about 95° C.; and/or: (iii) an adsorptive loading ratio for 1-pentanol over water of at least about 1 at about 10° C. to about 95° C.; and/or the cross-linked polymer optionally has an adsorptive loading ratio for isobutanol over water of at least about 1 at about 10° C. to about 50° C.

Embodiment 2

The adsorbent material of any of embodiment 1, wherein the ZIF material comprises optionally substituted benzimidazole linkers, such as ZIF-7.

Embodiment 3

The adsorbent material of embodiments 1 or 2, wherein the ZIF material is selected from the group consisting of ZIF-7, ZIF-22, EMM-19 and EMM-19*.

Embodiment 4

The adsorbent material of any one of the previous embodiments, wherein $R^1$ and $R^2$ are independently selected from the group consisting to of hydrogen; $C_1$-$C_3$-alkyl; an aryl selected from the group consisting of phenyl, naphthyl and indolyl; $C(R^3)_3$ in which each $R^3$ is independently hydrogen or aryl selected from the group consisting of phenyl, naphthyl and indolyl; or, taken together, $R^1$ and $R^2$ form a monocyclic, bicyclic or tricyclic aromatic hydrocarbon.

Embodiment 5

The adsorbent material of any one of the previous embodiments, wherein $R^1$ and $R^2$ are independently selected from the group consisting of hydrogen; $C_1$-$C_2$-alkyl; phenyl; $C(R^3)_3$ in which each $R^3$ is independently hydrogen or phenyl; or, taken together, $R^1$ and $R^2$ form a monocyclic or tricyclic aromatic hydrocarbon.

Embodiment 6

The adsorbent material of any one of the previous embodiments, wherein the cross-linked polymer comprises multiple monomers containing a moiety selected from the group consisting of benzene, toluene, ethyl benzene, naphthalene, 1,1'-biphenyl, diphenylmethane, tetraphenylmethane, triphenylmethane and triptycene, particularly the cross-linked polymer comprises multiple monomers containing benzene.

Embodiment 7

The adsorbent material of any one of the previous embodiments, wherein the ZIF material is selected from the group consisting of ZIF-7, ZIF-22, EMM-19 and EMM-19*; and $R^1$ and $R^2$ are independently selected from the group consisting of hydrogen; $C_1$-$C_2$-alkyl; phenyl; $C(R^3)_3$ in which each $R^3$ is independently hydrogen or phenyl; or, taken together, $R^1$ and $R^2$ form a monocyclic or tricyclic aromatic hydrocarbon.

Embodiment 8

A method for separating at least one organic compound from a solution (e.g., aqueous or non-aqueous), wherein the method comprises: contacting the solution with an adsorbent material according to any one of the previous embodiments.

Embodiment 9

The method of embodiment 8, wherein the at least one organic compound is present in the solution in a concentration of about 0.02 wt. % to about 10 wt. % or about 0.5 wt. % to about 5 wt. %.

Embodiment 10

The method of embodiment 8 or 9, wherein the adsorbent material is present in an amount capable of lowering the concentration of the at least one organic compound in the solution to about 0.9 wt. % or less or about 0.001 wt. % or less.

Embodiment 11

The method of embodiment 8, 9 or 10, wherein the solution is aqueous and/or the at least one organic compound is an alcohol (e.g., methanol, ethanol, propanol, butanol and pentanol).

Embodiment 12

The method of embodiment 8, 9, 10 or 11, wherein the ZIF material is present in an amount capable of lowering the concentration of ethanol in the aqueous solution to about 0.9 wt. % or less or about 0.001 wt. % or less and/or the cross-linked polymer is present in amount capable of lowering the concentration of isobutanol in the aqueous solution to about 0.9 wt. % or less or about 0.001 wt. % or less.

Embodiment 13

A method of producing biofuel, wherein the method comprises: hydrolyzing a biomass to form sugars; fermenting the sugars to produce an aqueous solution comprising one or more alcohols; and separating the one or more alcohols from the aqueous solution by contacting the aqueous solution with the adsorbent material according to any one of embodiments 1-7.

Embodiment 14

The method of embodiment 13, wherein the one or more alcohols are selected from the group consisting of methanol, ethanol, propanol, butanol and pentanol.

Embodiment 15

The method of embodiment 13 or 14, further comprising regenerating the adsorbent material, for example, heating the adsorbent material to a temperature of at least about 100° C. for at least about 1 hour.

EXAMPLES

The following examples are merely illustrative, and do not limit this disclosure in any way.

Example 1—Single Component Adsorption Isotherms for ZIF-7

Figure 2:
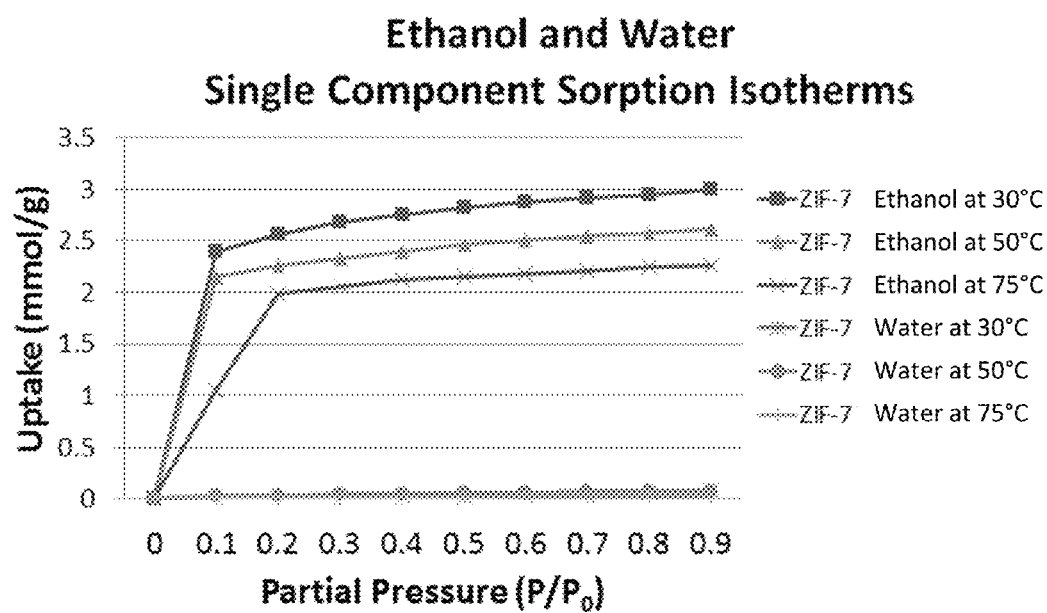
FIG. 2 illustrates ethanol and water single component adsorption isotherms for ZIF-7.
Figure 3:
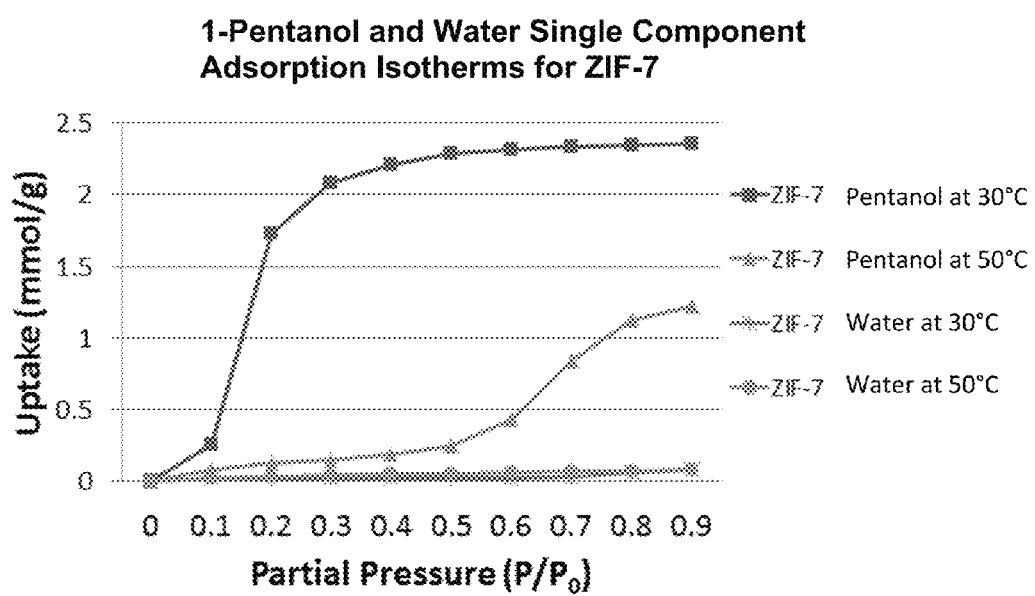
FIG. 3 illustrates 1-pentanol and water single component adsorption isotherms for ZIF-7.

Single component adsorption isotherms for ZIF-7 in mixtures of methanol and water, ethanol and water, and pentanol and water were determined. ZIF-7 was synthesized in a solvent mixture of acetonitrile (MeCN) and triethylamine (TEA) according to the procedure provided in U.S. Pat. Nos. 8,907,102, 8,920,541 and/or 8,636,969. The isotherms were determined using a TA Instruments Q5000 TGA with a modified gas/vapor delivery system. Prior to testing, the ZIF sample was prepared in situ by heating in an inert atmosphere to ~150° C. and holding for ~90 minutes before cooling to the sorption temperature. This established a "dry wt." as the basis for the uptake measurement. During the respective tests samples were held at the indicated sorption temperatures (e.g., ~30° C., ~50° C., ~75° C.). The vapor (e.g., methanol, ethanol, water, etc.) wa delivered to the sample at a fixed temperature, via a bubbler and through a temperature controlled glass condenser to establish the vapor pressure. The ultimate experimental condition, or $P/P_0$, was set by a combination of the vapor flow and an inert makeup flow that, together, total ~100%, which was ~100 cc/min. The test was performed at atmospheric pressure. Sample size ranged from ~3 to ~15 mg in size The isotherms are shown in FIGS. 1-3. The step change in adsorption isotherms shown in FIGS. 1-3 resulted from the structural change of ZIF-7 from np to lp. The ZIF-7 selectivity at various partial partials and temperatures is shown below in Tables 1-3.

TABLE 1

ZIF-7 Methanol/Water Selectivity

| Partial pressure | ~30° C. | ~50° C. | ~75° C. |
|---|---|---|---|
| ~0.1 | ~19.1 | ~7.9 | ~4 |
| ~0.2 | ~84.6 | ~9.8 | ~6.5 |
| ~0.3 | ~111.4 | ~11.5 | ~8.5 |
| ~0.4 | ~117.4 | ~15.3 | ~11 |
| ~0.5 | ~123.2 | ~36.6 | ~11.9 |
| ~0.6 | ~117.5 | ~39.8 | ~12.1 |
| ~0.7 | ~80.8 | ~35.7 | ~14.2 |
| ~0.8 | ~49.8 | ~32.8 | ~16.3 |
| ~0.9 | ~39.0 | ~31.9 | ~18.3 |

TABLE 2

ZIF-7 Ethanol/Water Selectivity

| Partial pressure | ~30° C. | ~50° C. | ~75° C. |
|---|---|---|---|
| ~0.1 | ~108.6 | ~84.4 | ~53 |
| ~0.2 | ~116.4 | ~66.9 | ~99.5 |
| ~0.3 | ~121.8 | ~56.0 | ~103 |
| ~0.4 | ~125 | ~51.0 | ~106 |
| ~0.5 | ~128.2 | ~45.7 | ~102.4 |
| ~0.6 | ~119.6 | ~43.8 | ~90.8 |
| ~0.7 | ~81.1 | ~38.6 | ~92.1 |
| ~0.8 | ~49.2 | ~35.1 | ~93.8 |
| ~0.9 | ~38.0 | ~34.1 | ~94.2 |

TABLE 3

ZIF-7 Pentanol/Water Selectivity

| Partial pressure | ~30° C. | ~50° C. |
|---|---|---|
| ~0.1 | ~11.8 | ~3.1 |
| ~0.2 | ~78.6 | ~3.8 |
| ~0.3 | ~94.5 | ~3.6 |
| ~0.4 | ~100.5 | ~4.0 |
| ~0.5 | ~104.1 | ~4.6 |
| ~0.6 | ~96.7 | ~7.5 |
| ~0.7 | ~65 | ~12.7 |
| ~0.8 | ~39.2 | ~15.4 |
| ~0.9 | ~29.9 | ~15.9 |

The determined capacity (thermaldynamic) for ZIF-7 was determined as follows:
- methanol and ethanol: uptake capacity was ~3.1 mmol/g at ~30° C., which is equivalent to ~6 alcohol molecules per SOD cage;
- 1-pentanol: uptake capacity was ~2.4 mmol/g at ~30° C., which is equivalent to ~4-5 alcohol molecules per SOD cage
- water: uptake capacity was ~0.08 mmol/g at ~30° C. and ~0.02 mmol/g at ~75° C.

The determined separation selectivity based on maximum adsorptive loading for ZIF-7 was determined as follows:
- Adsorptive loading of methanol over water was ~39 at ~30° C. and ~18 at ~75° C.;
- Adsorptive loading of ethanol over water was ~38 at ~30° C. and ~94 at ~75° C.;
- Adsorptive loading of 1-pentanol over water was ~30 at ~30° C.

Among methanol, ethanol and 1-pentanol, ethanol was adsorbed preferably into ZIF-7 based on single component sorption isotherms and was used as a main reference molecule to study multicomponent sorption and to further study ZIF-7's structural changes and adsorption.

Example 2—Analysis of ZIF-7 Adsorption Sites of Ethanol

Powder X-ray Diffraction (XRD) and carbon-13 and proton-1 nuclear magnetic resonance (13C and 1H 2D NMR) were performed on ZIF-7 without ethanol adsorbed therein and with ethanol adsorbed therein.

Figure 4A:
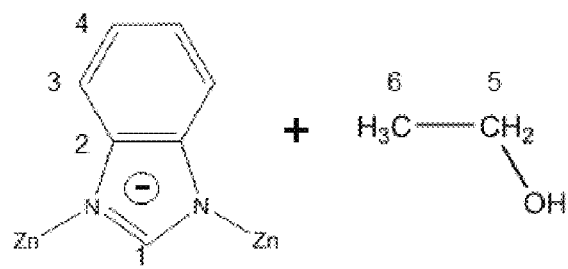
FIGS. 4a and 4b illustrate carbon-13 nuclear magnetic resonance ($^{13}$C-NMR-$^1$H 2D) spectrums for ZIF-7-narrow pore (ZIF-7-np) without ethanol and ZIF-7-large pore (ZIF-7-lp) with ethanol, respectively.
Figure 4A:
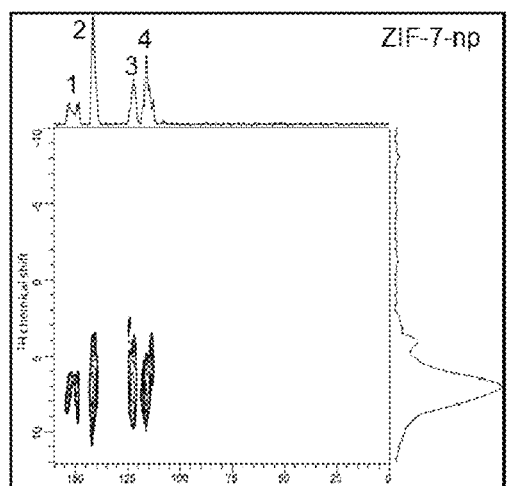
Figure 4B:
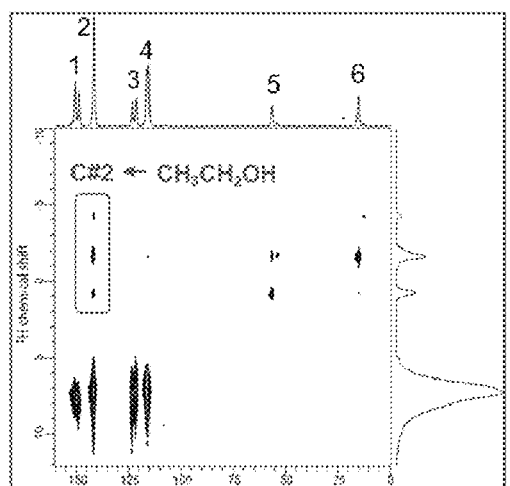
Figure 5:
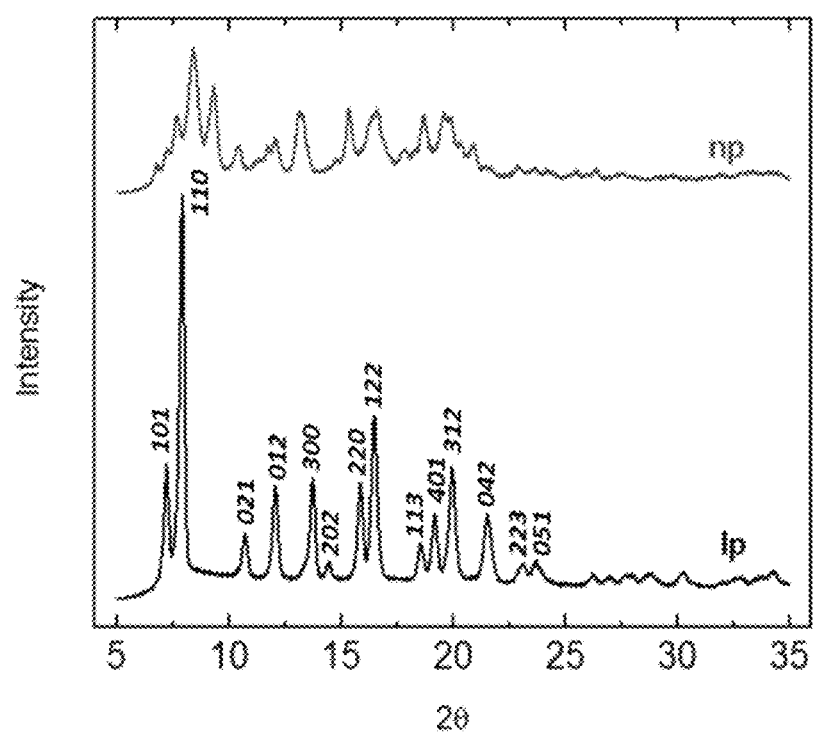
FIG. 5 illustrates a powder X-ray diffraction (XRD) pattern for ZIF-7-np and ZIF-7-lp.

Without ethanol molecules, ZIF-7 exists in its np phase ("ZIF-7-np") and with ethanol molecules ZIF-7 exists in its lp phase ("ZIF-7-lp with ethanol"). As shown in FIGS. 4 and 5, the two phases have distinctively different NMR spectrums and XRD patterns. In FIG. 4, the 2D 1H-13C cross-polarization solid state NMR spectrum for ZIF-7-lp with ethanol shows that the protons from ethanol were shifted to the negative field. Compared to the liquid-state ethanol, the significant 2-5 ppm negative shifts of absorbed ethanol demonstrated that strong interactions between ZIF-7 and ethanol caused the shift of ethanol protons. The strong cross peaks of ethanol protons and #2 carbon showed that ethanol sits inside the six membered ring and interacts strongly with #2 carbon. Under these interactions, ethanol molecules are no longer as liquid-state with fast molecular tumbling, but more rigid as solid-state, so that the ethanol signals can be collected in the cross-polarization solid-state 2D NMR spectrum. Further, in the $^1$H NMR spectrum for ZIF-7-lp with ethanol, the quantified carbon ratio indicates a linker: $CH_3CH_2OH$ ratio of ~2:1, which is equivalent to ~6 alcohol molecules per SOD cage. This is equivalent to a maximum uptake capacity of ~3.3 mmol/g, which closely matches the experimental sorption capacity from the determined single component isotherms. The difference can be attributed to gas phase (300 Torr) (for single component isotherms) and liquid phase (for NRM and XRD) of ethanol in each case.

Figure 6:
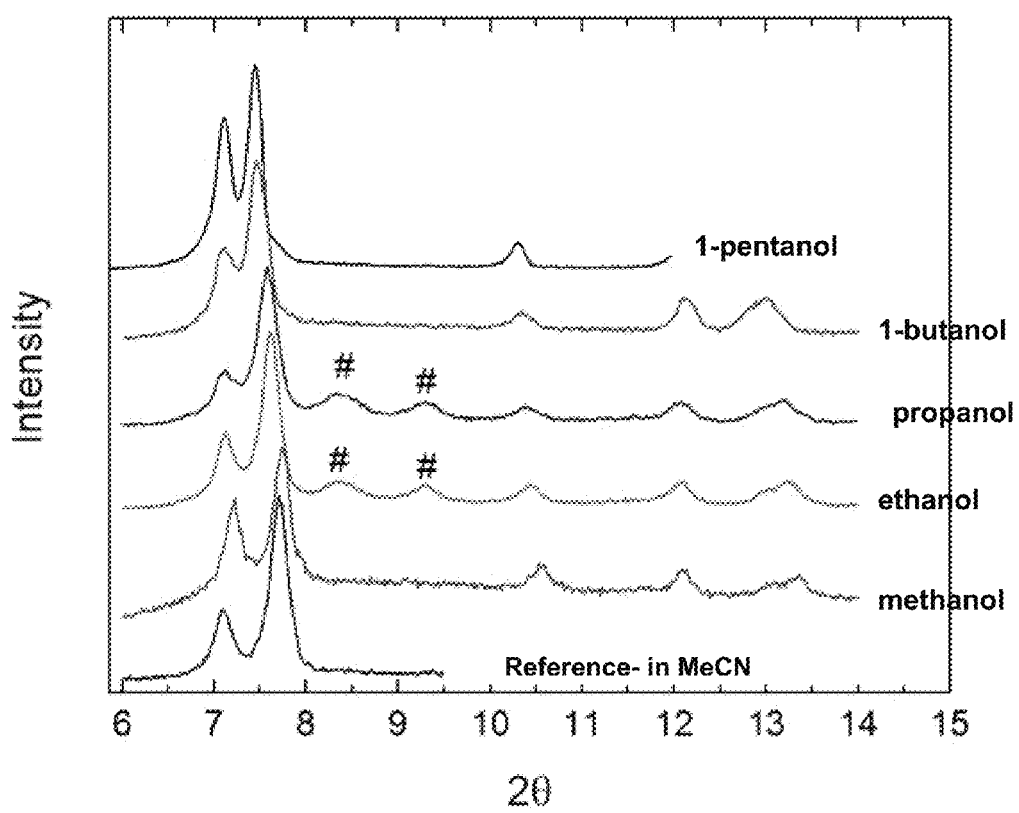
FIG. 6 illustrates a powder XRD pattern for ZIF-7 with linear $C_1$-$C_5$ alcohols and acetonitrile.
Figure 7:
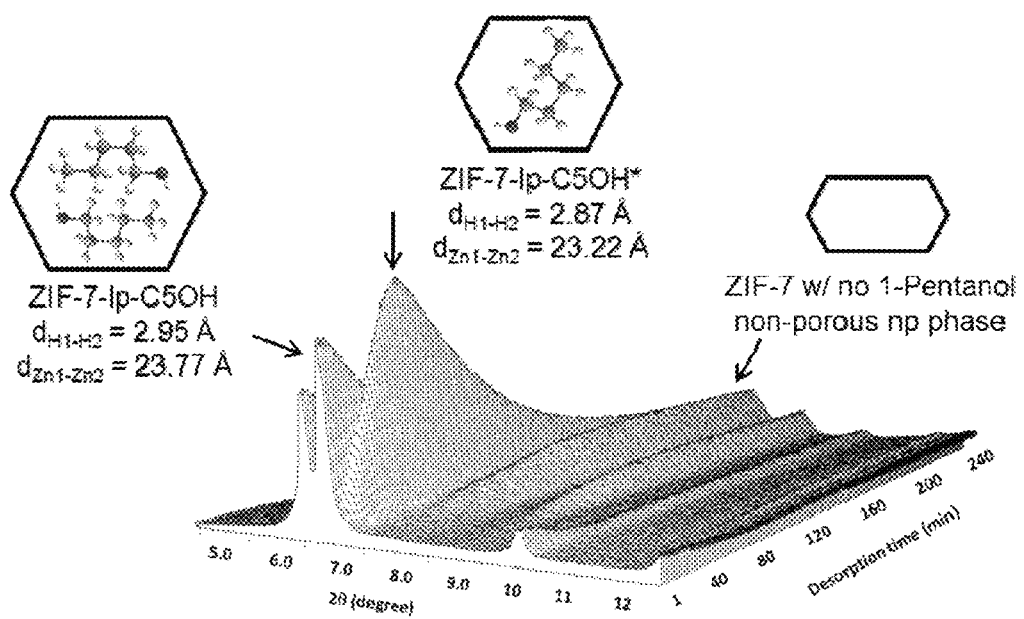
FIG. 7 illustrates in situ XRD patterns of ZIF-7 with different 1-pentanol loadings.

Example 3—Analysis of ZIF-7 Structural Changes Upon Adsorption of Different Alcohols Adsorption of each $C_1$-$C_5$ alcohol ($C_1OH$—$C_5OH$) in ZIF-7 was studied. Powder XRD was performed on each combination of ZIF-7 and $C_1$-$C_5$ alcohol. The XRD pattern is shown in FIG. 6. It was found that the unit cell dimension of ZIF-7 expanded to accommodate bigger alcohol molecules from $C_1OH$ to $C_5OH$. The unit cell dimension of ZIF-7-lp followed the trend of: ZIF-7-lp-$C_5OH$>ZIF-7-lp-$C_4OH$>ZIF-7-lp-$C_3OH$>ZIF-7-lp-$C_2OH$>ZIF-7-lp-$C_1OH$. The different XRD patterns of ZIF-7 with different 1-pentanol ($C_5OH$) loadings are shown in FIG. 7. Upon desorption of $C_5OH$ from ZIF-7-lp-$C_5OH$, an intermediate phase (ZIF-7-lp-$C_5OH^*$) was observed, which has a unit cell dimension similar to ZIF-7-lp-$C_2OH$. Hence the unit cell dimensions were as follows: ZIF-7-lp-$C_5OH$>ZIF-7-lp-$C_5OH^*$=ZIF-7-lp-$C_2OH$.

Example 4—Single Component Adsorption Isotherms for the Cross-Linked Polymer (1)

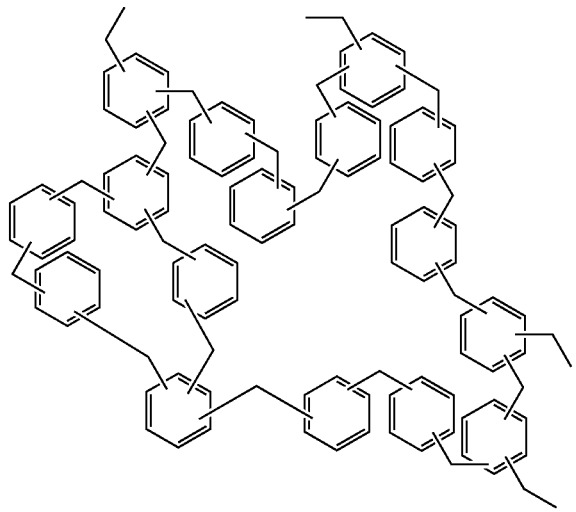

Figure 8:
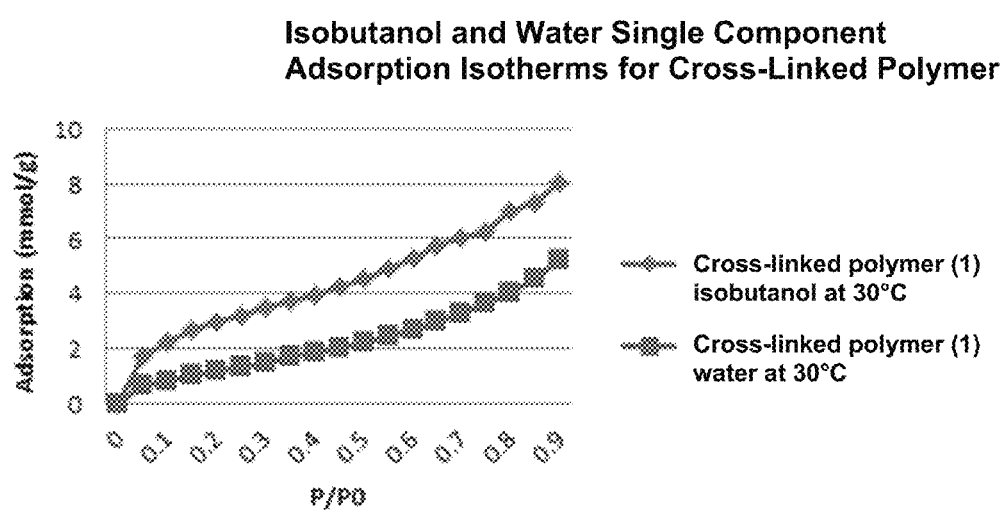
FIG. 8 illustrates isobutanol and water single component adsorption isotherms for cross-linked polymer (1).

Single component adsorption isotherms for the cross-linked polymer (1) shown above (made according to Woodward, R. et al. *J. Am. Chem. Soc.*, 136: 9028-9035 (2014)) in isobutanol and water were determined as described above. The isotherms are shown in FIG. 8.

The cross-linked polymer material continued to swell as it adsorbed either isobutanol or water. The maximum uptake for isobutanol at ~30° C. was ~8.03 mmol/g and the maximum uptake for water at ~30° C. was ~5.19 mmol/g, neither of which approached adsorption equilibrium. Within the measured range, the uptake curve displays a chemisorption behavior at $P/P_0$<0.1. When $P/P_0$ was over 0.1, the uptake curve is linearly dependent on the partial pressure indicating a gradual swelling mechanism of the cross-linked polymer (1) as it adsorbs alcohols and water.

As a result, the cross-linked polymer had an adsorptive loading ratio for isobutanol over water of ~1.5 molar at ~30° C. Further, the cross-linked polymer was able to lower the concentration of isobutanol in water from ~1.59 wt. % to ~0.02 wt. %, which was significantly better than both ZIF-7 and ZIF-8, which is surprising in light of the single component isotherms. Without being bound by theory, it is believed that due to competitive adsorption, isobutanol suppressed the adsorption of water and the actual selectivity increased.

Example 5—Separation of ~2-4 vol. % Alcohols from Water

The following examples were prepared as described below.

Preparation of Solutions

A ~2 vol. % ethanol in water solution was made by measuring out ~5 mL ethanol (using ~6 mL syringe) and diluting it to ~250 mL using deionized (DI) water and a volumetric flask. All ~2 vol. % solutions (isobutanol in water, 1:1 hexane:hexene, etc.) were prepared using this procedure.

For the ~4 vol. % ethanol solution, ~20 mL of ethanol was measured in a graduated cylinder, then diluted to ~500 mL using DI water in a volumetric flask.

For 1:1 alcohol solutions, ~15 mL of each alcohol (i.e., ethanol and isobutanol) was measured using a graduated cylinder to make a ~30 mL solution.

Separation Procedure

The desired amount of solid adsorbent (e.g., ZIF-7, ZIF-8, cross-linked polymer) in powder form was weighed and placed into a 3 dram vial. Using a syringe, ~2 mL of the stock solution, as prepared above, was added to the vial with the solid adsorbent. The vial was capped and mixed. Control solutions were prepared for each batch by adding ~2 mL of the stock solution to a vial and capping the vial.

If the solid adsorbent powder in the vials settled within ~1 hour and left a clear supernatant, the supernatant was pipetted out for analysis. If not, a filtration step was involved, where after shaking, the solution in the vial, a tightly rolled up a piece of cotton was placed into a thin part of a glass pipette, which acted as a filter. The pipette was put into the solution in the vial and the liquid was drawn through the pipette. This process was ~1 minute for small amounts of solid and up to ~30 minutes for the preparations with ~0.9 g of solid adsorbent. If the liquid remained cloudy, the pipetting was repeated on the filtered solution with a fresh filter pipette.

Example 5A—Separation of ~2 vol % or ~4 vol % Ethanol from Water Using ZIF-7

Different amounts of ZIF-7 (synthesized as described above) were added to ~2 ml of ethanol in water solution at concentrations of ~2 vol. % and ~4 vol. %. Mother liquid (i.e., original mixture of alcohol in water before ZIF-7 material is introduced) and the corresponding supernatant (i.e., liquid mixture after ZIF-7 material has been introduced into alcohol in water mixture following adsorption) were examined using either liquid NMR or gas chromotography. The concentration change was converted to an adsorption capacity (mmol/g) at each condition, as shown in the Table 4 below. The concentration of ethanol was lowered indicating a preferred selectivity of ethanol over water.

TABLE 4

| Ethanol Conc. (wt. %) | Volume (ml) | ZIF-7 (g) | Conc. After Ads. (wt. %)* | Ads. (mmol/g) |
| --- | --- | --- | --- | --- |
| ~1.59 (~2 vol. %) | ~2 | ~0.098 | ~1.18 | ~1.816 |
| ~1.59 | ~2 | ~0.297 | ~0.41 | ~1.726 |
| ~1.59 | ~2 | ~0.500 | ~0.24 | ~1.173 |
| ~1.59 | ~2 | ~0.902 | ~0.23 | ~0.656 |
| ~3.08 (~4 vol. %) | ~2 | ~0.100 | ~2.55 | ~2.290 |
| ~3.08 | ~2 | ~0.300 | ~1.75 | ~1.933 |
| ~3.08 | ~2 | ~0.499 | ~0.90 | ~1.902 |
| ~3.08 | ~2 | ~0.894 | ~0.27 | ~1.368 |

Data indicated that an equilibrium of ~0.25 wt. % ethanol in water was reached when ZIF-7 was used. The adsorption loading was ~2 mmol/g resulting in a linear decrease of ethanol concentration with increasing sorbent weight until the concentration approaches ~0.25 wt. %.

Additionally, the effects of temperature and time on adsorption were studied. Specifically, 0.5 grams of ZIF-7 was added to ~2 ml of ethanol in water solution at concentrations of ~2 vol. %. Mother liquid (i.e., original mixture of alcohol in water before ZIF-7 material is introduced) and the corresponding supernatant (i.e., liquid mixture after ZIF-7 material has been introduced into alcohol in water mixture following adsorption) were examined using liquid NMR. The concentration change was converted to an adsorption capacity (mmol/g) at each condition, as shown in the Table 5 below. The concentration change was measured at 0° C., room temperature ~25° C., and 50° C. for a contact time of less than two minutes. Additionally, the concentration change was measured at 0° C. for a contact time of greater than four hours. The concentration of ethanol was lowered more at higher temperatures and longer contact times indicating an improved preferred selectivity of ethanol over water as a function of temperature and contact time.

TABLE 5

| Ethanol Conc. (wt. %) | Volume (ml) | ZIF-7 (g) | Conc. After Ads. (wt. %)* | Ads. (mmol/g) |
| --- | --- | --- | --- | --- |
| ~1.71 (~2 vol. %) | ~2 | 0.500 | 1.31 (0° C. at <2 min contact) | ~0.348 |
| ~1.71 (~2 vol. %) | ~2 | 0.500 | 0.96 (r.t./<2 min contact) | ~0.652 |
| ~1.71 (~2 vol. %) | ~2 | 0.500 | 0.87 (50° C./<2 min contact) | ~0.730 |
| ~1.71 (~2 vol. %) | ~2 | 0.500 | 0.40 (0° C./>4 hrs contact) | ~1.139 |

Figure 9:
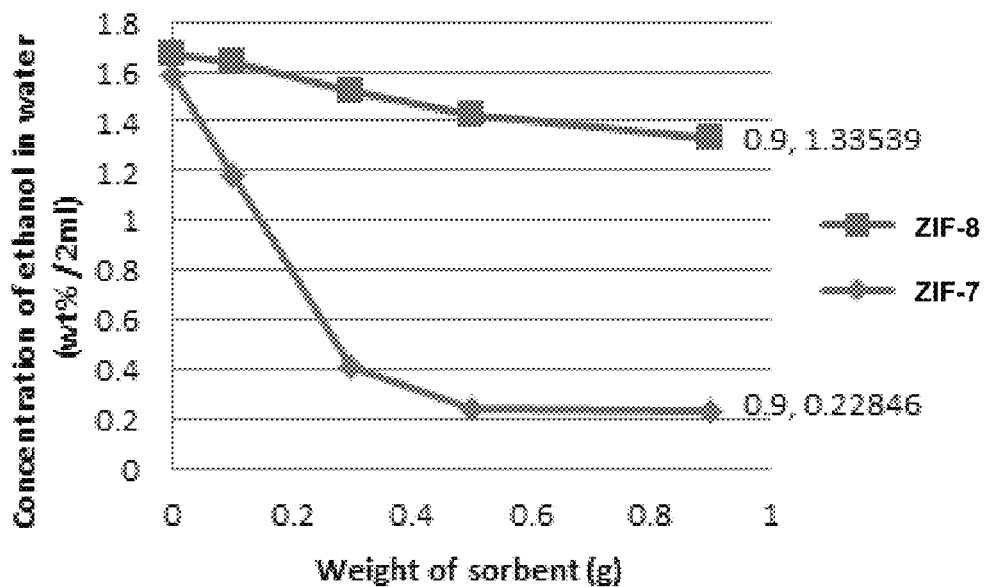
FIG. 9 illustrates the separation of ~1.7 wt. % ethanol from water with ZIF-7 and ZIF-8.
Figure 10:
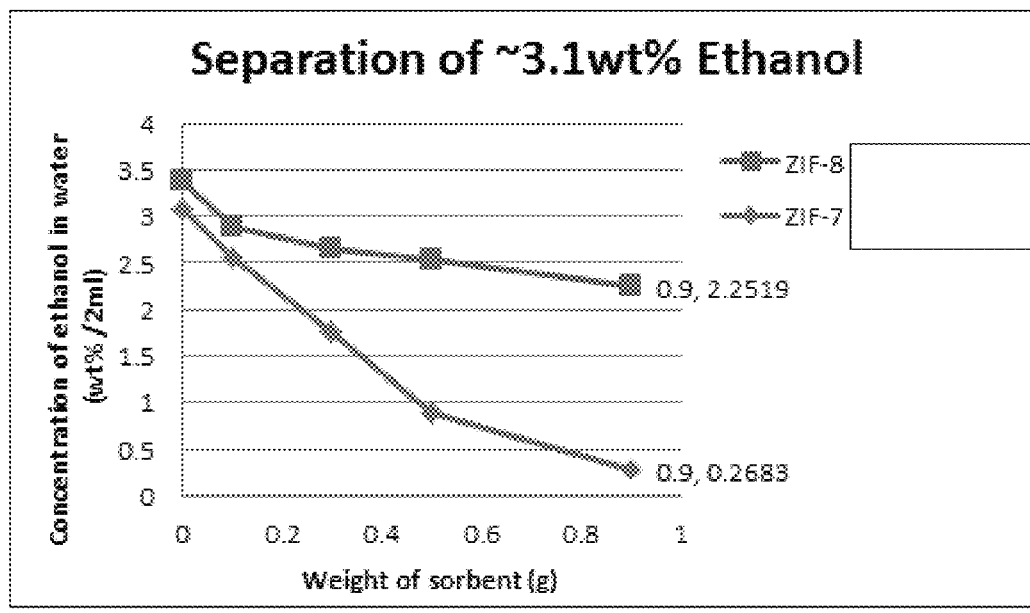
FIG. 10 illustrates the separation of ~3.1 wt. % ethanol from water with ZIF-7 and ZIF-8.

ZIF-8 (Basolite® Z1200 obtained from Sigma-Aldrich) was used as a reference material under the exact same conditions to compare the performance of ZIF-7. At ~2 vol. % case (~1.59 wt. % to ~1.75 wt. %), ~0.9 g of ZIF-8 was capable of lowering the concentration of ethanol to ~1.335 wt. %, while an equal weight of ZIF-7 was able to lower the concentration of ethanol to ~0.228 wt. %. The advantage of ZIF-7 over ZIF-8 was calculated based on the concentration difference: ~1.335/~0.228=~5.8 (2 vol. %), or ~2.252/~0.268=~8.4 (~4 vol. %). Thus, a five times enhancement in removing ethanol from water is indicated for ZIF-7 over ZIF-8. The comparison between ZIF-7 and ZIF-8 for separating ~1.7 wt. % ethanol and ~3.1 wt. % ethanol is shown in FIGS. 9 and 10, respectively. The cross-linked polymer (1) was also tested and performed slightly better than ZIF-8 but worse than ZIF-7.

For ~0.9 g of ZIF-7 in ~2 ml ~4 vol. % ethanol in water solution, regeneration of the ZIF-7 material was performed at ~150° C. for ~60 minutes (~1 hr), at ~150° C. for ~30 minutes and ~120° C. for ~60 minutes (~1 hr). Under such conditions, the ZIF-7 material was regenerated up to ~100% of its original capacity and selectivity, within the experimental errors which is +/−1% for capacity. At regeneration conditions of ~100° C. for ~60 minutes (~1 hr), the capacity was ~96% of its maximum capacity.

Example 5B—Separation of ~2 vol. % Isobutanol from Water Using Cross-Linked Polymer (1)

Different amounts of cross-linked polymer (1) were added to ~2 ml of ~2 vol. % isobutanol in water solutions. Mother liquid and the corresponding supernatant were examined using either liquid NMR or gas chromotography. The concentration change was converted to an adsorption capacity (mmol/g) at each condition, as shown in the Table 6 below.

TABLE 6

| butanol Conc. (wt. %) | Volume (ml) | Polymer (g) | Conc. Af. Ads. (wt. %) | Ads. (mmol/g) |
| --- | --- | --- | --- | --- |
| Iso-b: ~1.63 (~2 vol. %) | ~2 | ~0.100 | ~1.01 | ~1.682 |
| ~1.63 | ~2 | ~0.300 | ~0.33 | ~1.169 |
| ~1.63 | ~2 | ~0.499 | ~0.13 | ~0.808 |
| ~1.63 | ~2 | ~0.900 | ~0.05 | ~0.474 |
| n-b: ~1.64 (~2 vol. %) | ~2 | ~0.101 | ~0.96 | ~1.819 |
| ~1.64 | ~2 | ~0.301 | ~0.26 | ~1.239 |

TABLE 6-continued

| butanol Conc. (wt. %) | Volume (ml) | Polymer (g) | Conc. Af. Ads. (wt. %) | Ads. (mmol/g) |
|---|---|---|---|---|
| ~1.64 | ~2 | ~0.499 | ~0.10 | ~0.830 |
| ~1.64 | ~2 | ~0.899 | ~0.04 | ~0.482 |
| tert-b: 1.53 (~2 vol. %) | ~2 | ~0.099 | ~1.25 | ~0.758 |
| ~1.53 | ~2 | ~0.300 | ~0.76 | ~0.689 |
| ~1.53 | ~2 | ~0.500 | ~0.40 | ~0.611 |
| ~1.53 | ~2 | ~0.899 | ~0.19 | ~0.401 |

Figure 11:
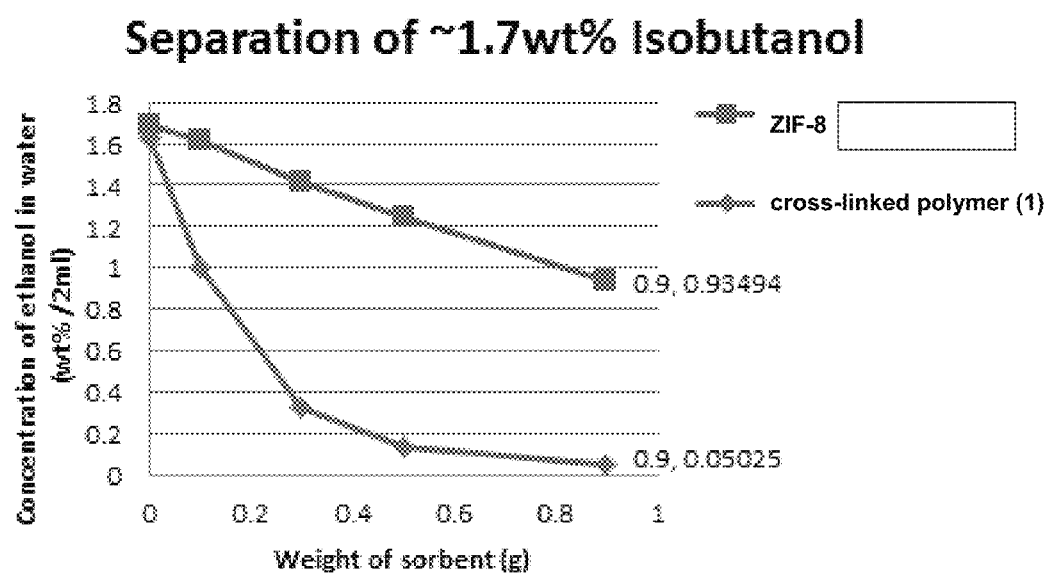
FIG. 11 illustrates the separation of ~1.7 wt. % isobutanol from water with the cross-linked polymer (1) and ZIF-8.

The data indicated that an equilibrium of ~0.05 wt. % isobutanol in water was reached when the cross-linked polymer was used. ZIF-8 (Basolite Z1200 obtained from Sigma-Aldrich) was used as a reference material under the exact same conditions to compare the performance of cross-linked polymer (1). At ~2 vol. % (~1.7 wt. %), ~0.9 g of ~ZIF-8 was capable of lowering the concentration of ethanol to ~0.935 wt. %, while an equal weight of cross-linked polymer was able to lower the concentration of ethanol to ~0.050 wt. %. The advantage of the cross-linked polymer (1) over ZIF-8 is calculated based on the concentration difference of ~0.935/~0.050=~18.7. The comparison between cross-linked polymer (1) and ZIF-8 for separating ~1.7 wt. % isobutanol is shown in FIG. 11. Similar tests were performed for other butanol isomers, e.g., n-butanol and tert-butanol. The cross-linked polymer was able to selectively adsorb all butanol isomers over water. ZIF-7 was also tested and it performed slightly better than ZIF-8 but worse than cross-linked polymer (1).

For ~0.9 g of cross-linked polymer (1) in ~2 ml ~2 vol. % isobutanol in water solution, regeneration of the cross-linked polymer (1) was performed at ~100° C. for ~60 minutes (~1 hr). Under such conditions, the cross-linked polymer (1) was regenerated up to ~100% of its original capacity and selectivity. When regeneration of the cross-linked polymer (1) was performed at ~80° C. for ~60 minutes (~1 hr), the cross-linked polymer (1) was regenerated up to ~94%. When regeneration of the cross-linked polymer (1) was performed at ~60° C. for ~60 minutes (~1 hr), the cross-linked polymer (1) was regenerated up to ~85%. When regeneration of the cross-linked polymer (1) was performed at ~100° C. for ~30 minutes, the cross-linked polymer (1) was regenerated up to ~88%.

Example 6—Separation of Alcohol Mixtures from Water or Toluene

The following examples were prepared as described below.
Preparation of Solutions
~5 mL of each alcohol were added together to form ~10 mL of a 1:1 volume alcohol mixture. This 1:1 alcohol mixture was then diluted to ~500 mL using water to form a ~2 vol. % solution.
Pretreatment of Solids
ZIF-7 (synthesized as described above) was dried at ~150° C. in $N_2$ for ~2 hours for each test to fully regenerate the sorbent material ZIF-7
Separation Procedure
The desired amount of ZIF-7 was weighed into a dram vial. Using a syringe, ~2 mL of the stock solution as prepared above was added to the vial with ZIF-7. The vial was capped and mixed. Control solutions were prepared for each batch by adding ~2 mL of the stock solution to a vial and capping the vial. Different amounts of ZIF-7, as shown in Table 7, for each of the below alcohol mixtures were tested.

TABLE 7

| 1 | ~2 mL as control |
| 2 | ~2 mL + ~0.1 g ZIF-7 |
| 3 | ~2 mL + ~0.3 g ZIF-7 |
| 4 | ~2 mL + ~0.5 g ZIF-7 |
| ~5 | ~2 mL + ~0.9 g ZIF-7 |

If the solid adsorbent powder in the vials settled within ~1 hour and left a clear supernatant, the supernatant was pipetted out for analysis. If not, a filtration step was involved, where after shaking the solution in the vial, a tightly rolled piece of cotton was placed into a thin part of a glass pipette, which acted as a filter. The pipette was put into the solution in the vial and the liquid was drawn through the pipette. This process was ~1 minute for small amounts of solid and up to ~30 minutes for the preparations with ~0.9 g of solid adsorbent. If the cotton filter worked adequately, there should only be clear liquid entering the pipette. Once enough sample for analysis had been obtained (normally ~1-1.5 mL), the pipette was removed from the solution, the cotton plug was removed, and the filtered liquid was transferred to a clean vial for analysis using either liquid NMR or gas chromatography. If the liquid remained cloudy, the pipetting was repeated on the filtered solution with a fresh filter pipette.

Example 6A—Separation of ~2 Vol. % Ethanol and 1-Pentanol from Water with ZIF-7

Equal volumes of ethanol and 1-pentanol were mixed into water resulting in a starting solution having ~0.299 mol. % of ethanol molecules, and ~0.157 mol. % of pentanol molecules with the remainder being water. Different amounts of ZIF-7 were placed in the starting solution and ethanol and 1-pentanol were selectively adsorbed from water.

Figure 12:
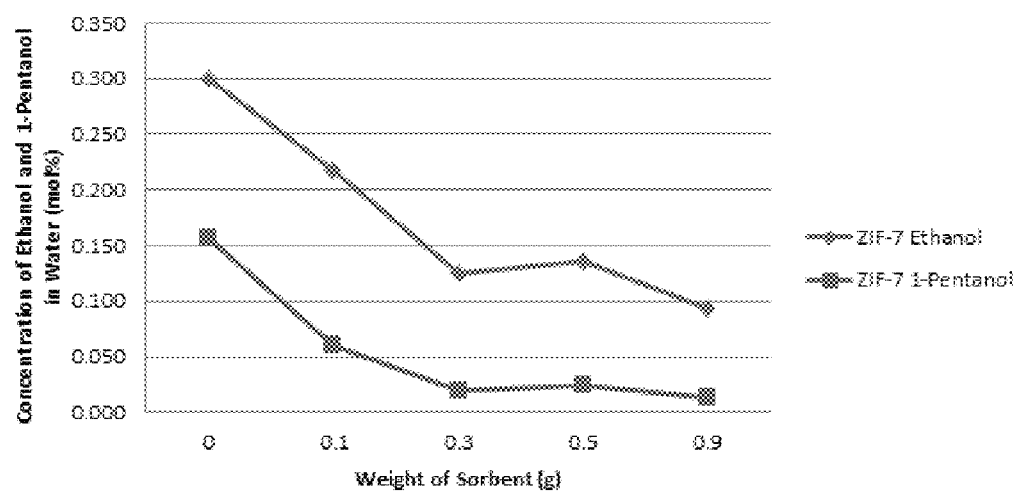
FIG. 12 illustrates the separation of ~2 vol. % ethanol and 1-pentanol from water with ZIF-7.

However, there was no significant difference between ethanol and pentanol adsorption. Specifically, with ~0.3 g to ~0.9 g of ZIF-7 in ~2 ml of 2 vol. % ethanol and 1-pentanol in water, ethanol concentration was lowered from ~0.299 mol. % to ~0.135-0.093 mol. %, and pentanol concentration was lowered from ~0.157 molar % to 0.025-0.013 mol. %. Thus, the trend to adsorb either ethanol or pentanol was similar. The selectivity of 1-pentanol over ethanol was ~0.7 as calculated from (0.157–0.013)/(0.299–0.0.093)=0.699. The separation of ~2 vol. % ethanol and 1-pentanol from water with ZIF-7 is shown in FIG. 12.

Example 6B—Separation of ~2 Vol. % 2-Methyl-1-Butanol/3-Methyl-2-Butanol and 1-Pentanol from Water with ZIF-7

It was evaluated whether branched alcohols can affect the selectivity of ZIF-7 at equilibrium. Two different branched alcohols, 2-methyl-1-butanol and 3-methyl-2-butanol, were compared separately and together with linear pentanol.

Figure 13:
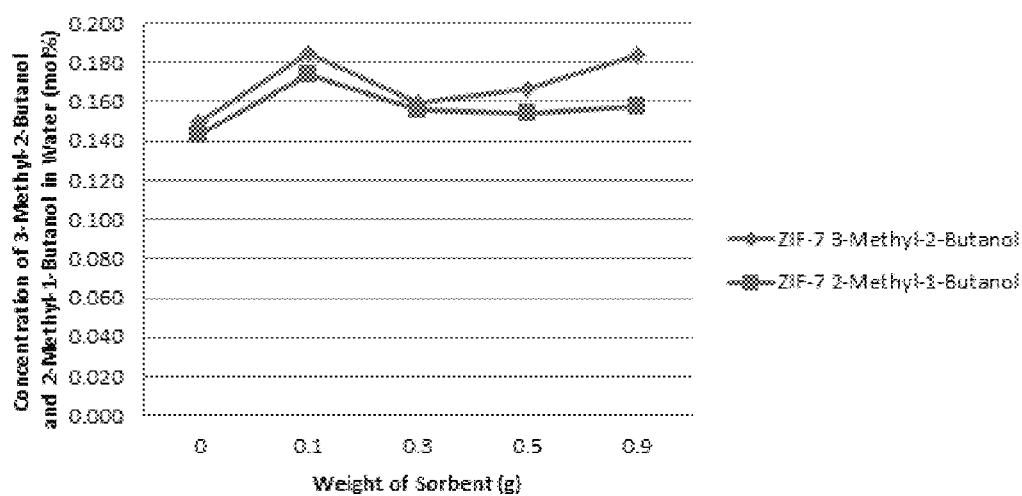
FIG. 13 illustrates the separation of 2 vol. % 2-methyl-1-butanol and 3-methyl-2-butanol from water with ZIF-7.

With the two branched alcohols, there appeared to be little adsorption by ZIF-7. The separation of ~2 vol. % 2-methyl-1-butanol and 3-methyl-2-butanol from water with ZIF-7 is shown in FIG. 13. The concentration of the solution was around 0.160 mol. % with or without ZIF-7. ZIF-7 is non-porous in its narrow pore (np) form (i.e., its natural low energy state). It is believed that the branched alcohols were too big to adsorb into this np phase of ZIF; hence the branched alcohols were not adsorbed and no change in concentration was observed.

Figure 14:
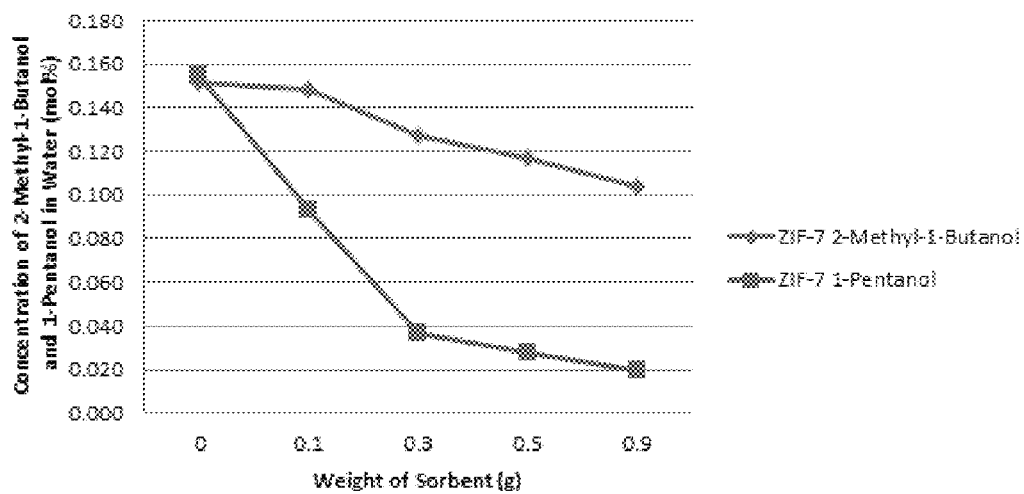
FIG. 14 illustrates the separation of ~2 vol. % 2-methyl-1-butanol and 1-pentanol from water with ZIF-7.

When an equal volume of 2-methyl-1-butanol and 1-pentanol were mixed into water, there was a difference in adsorption of 2-methyl-1-butanol. The separation of ~2 vol. % 2-methyl-1-butanol and 1-pentanol from water with ZIF-7 is shown in FIG. 14. 1-pentanol can be adsorbed in ZIF-7 whereby ZIF-7 is changed from np to lp structure. Thus, upon adsorption of 1-pentanol, ZIF-7 was in lp form thereby 2-methyl-1-butanol was adsorbed and replaced some 1-pentanol. ZIF-7 selectively adsorbed 2-methyl-1-butanol and 1-pentanol from water and lowered the concentration from 0.151/0.155 mol. % to 0.104/0.019 mol. % resulting in a selectivity of 1-pentanol/2-methyl-1-butanol of ~2.8 as calculated from (0.155−0.019)/(0.151−0.104)=2.89.

Figure 15:
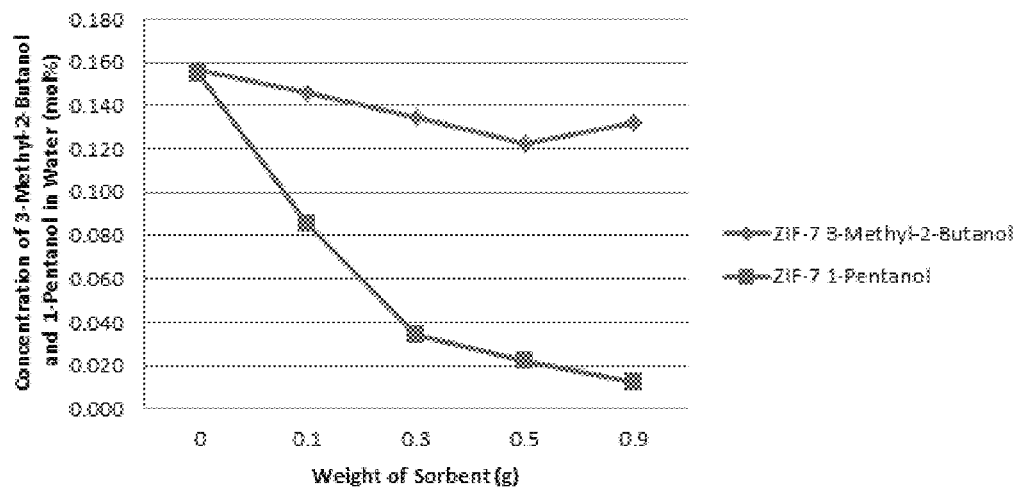
FIG. 15 illustrates the separation of ~2 vol. % 3-methyl-2-butanol and 1-pentanol from water with ZIF-7.

When an equal volume of 3-methyl-2-butanol and 1-pentanol were mixed into water, similar results occurred. The separation of ~2 vol. % 3-methyl-2-butanol and 1-pentanol from water with ZIF-7 is shown in FIG. 15. ZIF-7 selectively adsorbed 3-methyl-2-butanol and 1-pentanol from water and lowered the concentration from 0.157/0.155 mol. % to 0.132/0.012 mol. % resulting in a selectivity of 1-pentanol/2-methyl-1-butanol ~5.7 as calculated from (0.155−0.012)/(0.157−0.132)=5.72.

Example 6C—Separation of ~4 vol. % 2-Methyl-1-Butanol and Ethanol from Water with ZIF-7

Additionally, separation of an alcohol mixture of 2-methyl-1-butanol and ethanol in water was tested. ~2 mL of ~2-methyl-1-butanol and ~2 mL of ethanol were added together to form ~4 mL of a 1:1 volume mixture. This 1:1 mixture was then diluted to ~100 mL using water to form a ~4 vol. % solution. The separation procedure was performed as described above in Example 6.

Figure 16:
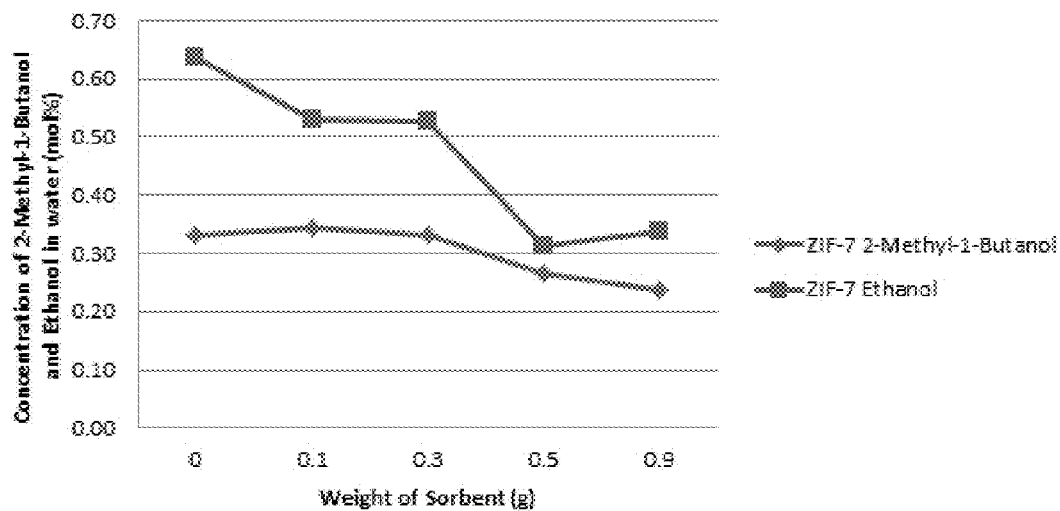
FIG. 16 illustrates the separation of ~4 vol. % 2-methyl-1-butanol and ethanol from water with ZIF-7.

The separation of ~4 vol. % 2-methyl-1-butanol and ethanol from water with ZIF-7 is shown in FIG. 16. Similar to 1-pentanol, upon adsorption of ethanol, ZIF-7 was in lp form and 2-methyl-1-butanol was adsorbed. The selectivity of ~0.9 g of ZIF-7 was ~3.3 as calculated by (0.64−0.34)/(0.33−0.24)=3.33.

Thus, it appears that at equilibrium, the adsorption selectivity of ZIF-7 for the abovementioned alcohols is a preference for ethanol>1-pentanol>2-methyl-1-butanol>3-methyl-2-butanol>water (Hexane or Toluene).

Example 6D—Separation of ~4 vol. % Hexane and Ethanol from Toluene

~2 mL of hexane and ~2 mL of ethanol were added together to form ~4 mL of a 1:1 volume mixture. This 1:1 mixture was then diluted to ~100 mL using toluene to form a ~4 vol. % solution.

Figure 17:
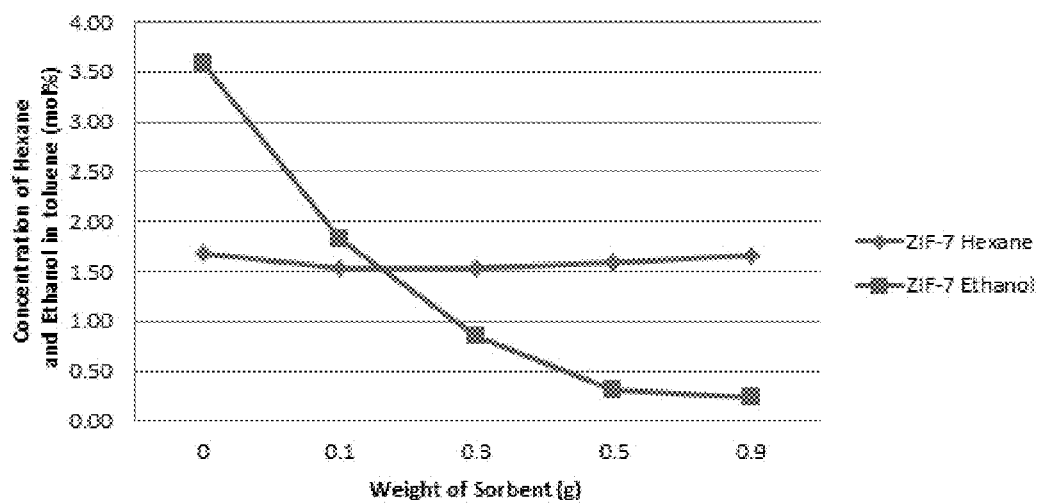
FIG. 17 illustrates the separation of ~4 vol. % hexane and ethanol from toluene with ZIF-7.

The separation of ~4 vol. % hexane and ethanol from toluene with ZIF-7 is shown in FIG. 17. Hexane was not adsorbed even when ethanol opened ZIF-7 to lp form. However, ethanol concentration significantly decreased with the amount of loading. The adsorption capacity for ethanol in hexane and toluene mixture is shown below in Table 8. The initial adsorption capacity was significant (~3.826 mmol/g) and the other adsorption capacities were closer to separation of ethanol in water.

TABLE 8

| Ethanol Conc. (wt. %) | Volume (ml) | ZIF-7 (g) | Conc. After Ads. (wt. %)* | Ads. (mmol/g) |
| --- | --- | --- | --- | --- |
| ~1.79 (~2 vol. %) | ~2 | ~0.1 | ~0.91 | ~3.826 |
| ~1.79 | ~2 | ~0.3 | ~0.43 | ~1.971 |
| ~1.79 | ~2 | ~0.5 | ~0.16 | ~1.417 |
| ~1.79 | ~2 | ~0.9 | ~0.12 | ~0.807 |

Example 7—Separation of ~4 vol. % Hexane and Hexene from Toluene

Figure 18:
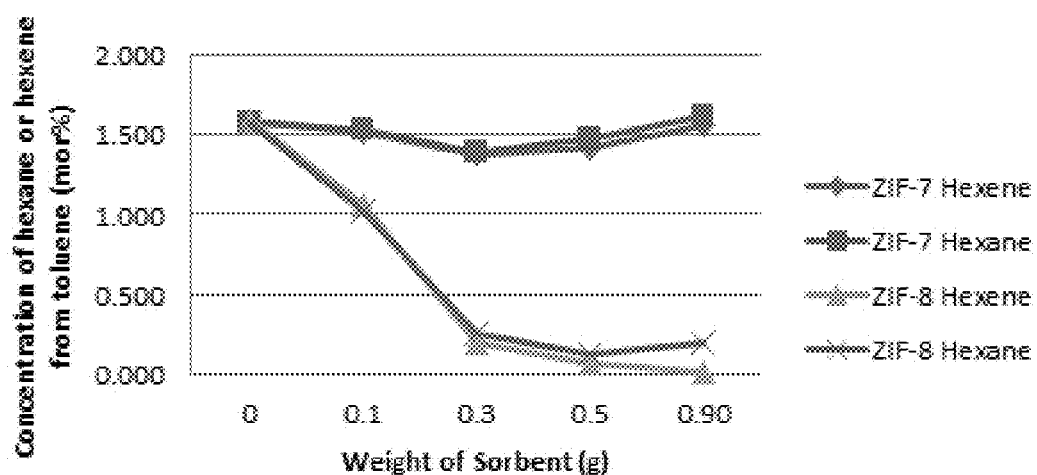
FIG. 18 illustrates the separation of ~4 vol. % hexane:hexene from toluene with ZIF-7 and ZIF-8.

Separation of ~4 vol. % hexane and hexene from toluene with ZIF-7 and ZIF-8 were studied. A 1:1 hexane:hexene mixture was made by combining ~5 mL of hexane with ~5 mL of hexene. Then ~4 mL of the 1:1 hexane:hexene mixture was diluted with ~100 mL of toluene to make a ~4 vol. % solution of hexane and hexene in toluene. ZIF-8 was able to selectively adsorb hexane or hexene over toluene and successfully decreased the concentration of both hexane and hexene from ~1.59 mol. % to ~0.1 mol. %. There was no significant selectivity between hexene and hexane at this concentration. The comparison between ZIF-7 and ZIF-8 for separating ~4 vol. % hexane:hexene from toluene is shown in FIG. 18.

What is claimed is:

1. An adsorbent material comprising:
   a ZIF-7 material having: an adsorptive loading ratio for methanol over water of at least about 1 at 10° C. to 95° C.; and
   a cross-linked polymer having a structure as below:

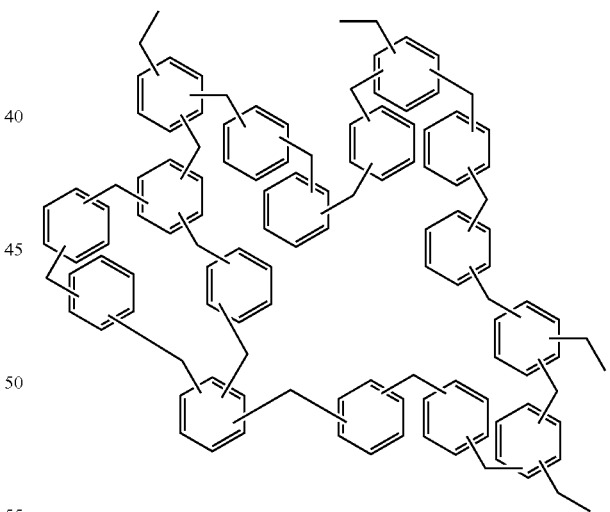

the cross-linked polymer having an adsorptive loading ratio for isobutanol over water of at least 1 at 10° C. to 50° C.

2. A method for separating at least one organic compound comprising an alcohol from an aqueous solution, wherein the method comprises:
   contacting the aqueous solution with an adsorbent material of claim 1.

3. The method of claim 2, wherein the alcohol is present in the aqueous solution in a concentration of 0.02 wt. % to 10 wt. %.

4. The method of claim 2, wherein the alcohol is present in the aqueous solution in a concentration of 0.5 wt. % to 5 wt. %.

5. The method of claim 2, wherein the adsorbent material is present in an amount capable of lowering the concentration of the alcohol in the aqueous solution to 0.9 wt. % or less.

6. The method of claim 2, wherein the adsorbent material is present in an amount capable of lowering the concentration of the alcohol in the aqueous solution to about 0.001 wt. % or less.

7. The method of claim 2, wherein the alcohol is selected from the group consisting of methanol, ethanol, propanol, butanol and pentanol.

* * * * *